(12) United States Patent
Peng et al.

(10) Patent No.: US 7,273,904 B2
(45) Date of Patent: Sep. 25, 2007

(54) NANOCRYSTALS IN LIGAND BOXES EXHIBITING ENHANCED CHEMICAL, PHOTOCHEMICAL, AND THERMAL STABILITY, AND METHODS OF MAKING THE SAME

(75) Inventors: Xiaogang Peng, Fayetteville, AR (US); Haiyan Chen, Fayetteville, AR (US); Wenzhou Guo, Cupertino, CA (US); Y. Andrew Wang, Fayetteville, AR (US)

(73) Assignee: The Board of Trustees of the University of Arkansas, Little Rock, AR (US)

( * ) Notice: Subject to any disclaimer, the term of this patent is extended or adjusted under 35 U.S.C. 154(b) by 329 days.

(21) Appl. No.: 10/679,247

(22) Filed: Oct. 3, 2003

(65) Prior Publication Data
US 2005/0004293 A1    Jan. 6, 2005

Related U.S. Application Data

(60) Provisional application No. 60/417,796, filed on Oct. 3, 2002.

(51) Int. Cl.
*C08K 3/30* (2006.01)
*H01L 21/76* (2006.01)
*C01B 21/064* (2006.01)

(52) U.S. Cl. .............. 524/439; 525/420; 438/403; 438/404; 423/290; 423/299; 423/325; 423/344; 423/409; 423/440; 423/491; 423/509; 423/566.1; 423/592.1

(58) Field of Classification Search ............... 423/290, 423/299, 325, 344, 409, 440, 491, 509, 566.1, 423/592.1; 438/403, 404; 525/420; 524/439
See application file for complete search history.

(56) References Cited

U.S. PATENT DOCUMENTS

| | | | |
|---|---|---|---|
| 5,260,957 A | 11/1993 | Hakimi et al. | |
| 5,427,767 A | 6/1995 | Kresse et al. | |
| 5,565,215 A | 10/1996 | Gref et al. | |
| 5,990,479 A | 11/1999 | Weiss et al. | |

(Continued)

FOREIGN PATENT DOCUMENTS

EP    09 977 212 A2    2/2000

OTHER PUBLICATIONS

Daniel et al., Gold Nanoparticles Contaiing Redox-active Supramolecular Dendrons that recognize H2PO4—Chemical Communications, No. 19, Sep. 18, 2001, p. 2000-2001.

(Continued)

*Primary Examiner*—Porfirio Nazario-Gonzalez
(74) *Attorney, Agent, or Firm*—J. Clinton Wimbish; Kilpatrick Stockton

(57) ABSTRACT

Dendron ligands or other branched ligands with cross-linkable groups were coordinated to colloidal inorganic nanoparticles, including nanocrystals, and substantially globally cross-linked through different strategies, such as ring-closing metathesis (RCM), dendrimer-bridging methods, and the like. This global cross-linking reaction sealed each nanocrystal within a dendron box to yield box-nanocrystals which showed dramatically enhanced stability against chemical, photochemical and thermal treatments in comparison to the non-cross-linked dendron-nanocrystals. Empty dendron boxes possessing a very narrow size distribution were formed by the dissolution of the inorganic nanocrystals contained therein upon acid or other etching treatments.

10 Claims, 20 Drawing Sheets

U.S. PATENT DOCUMENTS

| | | | |
|---|---|---|---|
| 6,074,979 | A | 6/2000 | Hagemeyer et al. |
| 6,194,213 | B1 | 2/2001 | Barbera-Guillem |
| 6,326,144 | B1 | 12/2001 | Bawendi et al. |
| 6,344,272 | B1 | 2/2002 | Oldenburg et al. |
| 6,576,291 | B2 | 6/2003 | Bawendi et al. |
| 6,607,829 | B1 | 8/2003 | Bawendi et al. |
| 6,617,583 | B1 | 9/2003 | Bawendi et al. |
| 7,153,703 | B2 * | 12/2006 | Peng et al. ............ 436/524 |
| 2002/0066401 | A1 | 6/2002 | Peng et al. |
| 2002/0071952 | A1 | 6/2002 | Bawendi et al. |
| 2004/0101976 | A1 | 5/2004 | Peng et al. |

OTHER PUBLICATIONS

Kim et al., "Novel Dendron-stablized Gold Nnanoparticles with High Stability and Narrow Size Distribution," Chemical Communications, vol. 7, No. 7, Mar. 21, 2001, pp. 667-668.

Wang et al., "Dendron-Controlled Nucleation and Growth of Gold Nanoparticles", Angewandte Chemi International Edition, vol. 40, No. 3, Feb. 2, 2001, pp. 549-552.

PCT Search Report, corresponding to PCT/US03/31461, mailed on Feb. 28, 2005.

Derwent Publication #XP002262148, Sep. 18, 2002, Abstract.

* cited by examiner

G3-(hydroxamide)-CH=CH₂

G3-(carboxylic)-CH=CH₂

G2-(amine)-ester

G3-(thiol)-CH=CH₂

G3-(di-amine)-OH

G3-(thiol)-OH

G3-(di-carboxylic)-OH/PEG

G4-(di-carboxylic)-CH=CH₂/PEG

Part I

Part II

NANOCRYSTALS IN LIGAND BOXES EXHIBITING ENHANCED CHEMICAL, PHOTOCHEMICAL, AND THERMAL STABILITY, AND METHODS OF MAKING THE SAME

PRIOR RELATED U.S. APPLICATION DATA

This application claims priority to U.S. patent application Ser. No. 60/417,796, filed Oct. 3, 2002, which is incorporated herein in its entirety.

TECHNICAL FIELD OF THE INVENTION

The present invention is related to methods of using organic ligands to stabilize nanocrystals, as well as nanocrystals stabilized by these ligands. More specifically, the present invention provides new compositions and methods involving ligands to enhance the chemical, photochemical and thermal stability of colloidal nanocrystals.

BACKGROUND OF THE INVENTION

Colloidal nanoparticles are nanometer-sized solid particles which are of interest for advanced materials applications. Generally, colloidal nanoparticles include colloidal nanocrystals as well as amorphous particles, and can comprise either inorganic or organic solids. For simplicity, inorganic nanocrystals are discussed as the representatives of nanometer-sized solids. The term "nanometer-sized" is typically used to refer to particles with an approximate size range between about 1 nm to about 1000 nm in diameter (one nanometer is $10^{-9}$ meter). More typically, "nanometer-sized" refers to an approximate size range between about 1 nm to about 100 nm in diameter.

Usually, nanocrystals are thermodynamically metastable and typically need kinetic stabilization with a monolayer of organic ligands, typically referred to as capping groups, surfactants, stabilizers, and the like. These organic ligands function by having at least one binding site with which to bind the surface atoms of the nanocrystals, while the remaining portion of the ligand molecules provides steric isolation between nanocrystals.

Organic dendrons are regularly branched organic molecules starting from a focal point or molecular branching point, which can be used as ligands for nanocrystals. For simplicity, the term dendron is used to refer to any organic ligand that is substantially branched. With organic dendrons, the molecular focal point typically constitutes the site at which the ligand binding occurs while the periphery constitutes the organic groups that provide steric protection. The number of branching points from the focal point to the terminal groups of the dendron is used to characterize these ligands and is referred to as the number of generations of the dendrons. For instance, generation 3 (G3) dendrons refers to dendrons with three branching points from the focal point to the terminal groups of the dendrons.

Colloidal nanocrystals have generated great fundamental interest in recent years and continue to exhibit tremendous promise for developing advanced materials for a variety of important technical applications. The size-dependent emission is probably the most attractive property of semiconductor nanocrystals. For example, differently sized CdSe nanocrystals can be prepared that emit from blue to red with very pure color. These nanocrystal-based emitters can be used for many purposes, such as light-emitting diodes, lasers, biomedical tags, and the like. Further, magnetic nanocrystals can be used as enhancing agents for magnetic resonance imaging (MRI) in the medical diagnostics industry.

Current research and development activities in colloidal nanocrystals remain hindered by the paucity of reliable processing chemistry. Recent developments in the synthesis of semiconductor, metal, and oxide nanocrystal systems, have placed the need for better processing chemistry in an even more urgent position. The processibility of colloidal nanocrystals is related to the stability of the nanocrystal-ligand complex, which it turn is related to the nature and structure of the surface ligand monolayer, the interface between the inorganic core and the organic ligand monolayer, and the structure of the surface of the inorganic nanocrystals themselves. Yet, knowledge regarding the structure of inorganic nanocrystal surface, the nature of the nanocrystal-ligand interface, and the dynamics and structure of the ligands within the monolayer is limited.

An example of the importance in obtaining stable nanocrystal-ligand complexes is seen in the lifetime of the light emitting diodes (LEDs) based on semiconductor nanocrystals. Presently, this attainable lifetime is relatively short, which is likely the result of the thermal dissociation of organic ligands from the nanocrystal surface during operation of the LED device. Further, the troublesome conjugation chemistry related to promising biological labeling applications using semiconductor nanocrystals has been also found to be associated with the detachment of the organic ligands from the nanocrystal surface. Additionally, the long-pursued enhancement effect of magnetic nanocrystals for magnetic resonance imaging is still in its infancy because of the instability of the ligands on the surface of the nanocrystals.

Two types of stability/instability issues related to nanocrystal/ligand complexes have been identified. Type I instability arises when the organic ligands dissociate from the inorganic core, and the nanocrystal/ligand complex is thus destroyed. In solution, this type instability results in uncontrollable chemical properties of the outer surface of the ligand monolayer and the detachment of the desired chemical/biochemical functions from the inorganic core. In many cases, this Type I instability also induces precipitation of the nanocrystals. In both solid state and in solution, dissociation of the organic ligands and the inorganic core often causes undesired variations of the properties of nanocrystals, such as decrease of either photoluminescence or electroluminescence brightness. Type II instability is associated with the inorganic core of the nanoparticle or nanocrystal being subject to oxidation, etching, and even complete dissolution. Thus, Type II instability normally defeats the function of the original nanocrystal/ligand complex.

Therefore, what is needed are new processing methods to impart and maintain greater stability to the nanocrystal/ligand complex. Both Type I instability resulting from dissociation of organic ligands from the inorganic core, and Type II instability arising from the chemical oxidation, etching, or dissolution of the inorganic core following ligand dissociation should be addressed. Nanocrystal stability is closely associated with the nature and structure of the surface ligand monolayer, the interface between the inorganic core and the organic ligand monolayer, and the structure of the surface of the inorganic nanocrystals themselves, therefore all these aspects of nanocrystal stability should be addressed. If possible, these new processing methods would be applicable to enhance the thermal stability, the redox stability, and the photolytic stability of the nanocrystal/ligand complex.

SUMMARY OF THE INVENTION

The present invention addresses the current limitations in nanocrystal stability by affording stable nanocrystal-ligand complexes though improved stability of both inorganic nanocrystal core as well as the organic ligand monolayer. New methods for enhancing stability and new compositions of nanocrystals are provided herein.

Typically, semiconductor nanocrystals were employed because of their general interest, easy detection and relatively better established synthetic and ligand chemistry, however, the methods described herein are equally applicable to nanocrystals that are not semiconductors. Typically, the stability of the CdSe nanocrystal core was enhanced by the epitaxial growth of a thin layer of CdS on their surface. Such core-shell structures can improve the photochemical stability of CdSe nanocrystals by the confinement of the photo-generated charges inside the core material. Additionally, the enhanced stability of the ligand monolayer was achieved by cross-linking substantially all the surface ligands of each nanocrystal.

As will be understood from the description of this invention, the cross-linking of surface ligands of a nanocrystal results in enhanced stability of the ligand sheath surrounding the nanocrystal, as well as the nanocrystal-ligand complex as a whole. Accordingly, one aspect of this invention is improving and enhancing the cross-linking of these ligands to achieve more stable nanocrystal-ligand complexes. To achieve substantial cross-linking, it is not necessary that all of the cross-linkable sites of each ligand engage in a cross-linking reaction. Typically, substantial cross-linking implies that most of the ligands of the nanocrystal-ligand complex engage in cross-linking reactions that serve to enhance and improve stability.

One aspect of this invention is a composition referred to as a "box-nanocrystal," comprising a nanocrystal core usually in the size range between 1 and 100 nm and a plurality of dendron ligands coordinated to the nanocrystal core that are substantially cross-linked. The nanocrystal core of the box-nanocrystal can comprise a metal, an elemental non-metal, an organic compound, a metal oxide, a metal chalcogenide, a metal pnictogen, a metal halide, an alloy, a mixed metal oxide, or a combination thereof. Further, the nanocrystal core of the box-nanocrystal may comprise a boride, a carbide, a silicide, a nitride, a phosphide, an arsenide, an oxide, a sulfide, a selenide, a telluride, a fluoride, a chloride, a bromide, an iodide, or a combination thereof. When the nanocrystal core is an oxide material, then the nanocrystal core may comprises an oxide of silicon, aluminum, titanium, zirconium, iron, nickel, cobalt, manganese, ruthenium, antimony, tin, cerium, barium, vanadium, chromium, lead, copper, indium, yttrium, zinc, mixed oxides thereof, or combinations thereof.

Another aspect of this invention is a similar composition referred to as a "box-nanoparticle," which is a generic term for a composition comprising a crystalline or a non-crystalline nanoparticle core, usually in the size range between 1 and 100 nm, and a plurality of dendron ligands coordinated to the nanoparticle core that are substantially cross-linked. Thus, a box-nanocrystal is a box-nanoparticle having a nanocrystal core. The nanoparticle core of the box-nanoparticle may comprise the same types of materials as those specifically disclosed herein for the box-nanocrystal, including but not limited to, a metal, an elemental non-metal, an organic molecule, a metal oxide, a metal chalcogenide, a metal pnictogen, a metal halide, an alloy, a mixed metal oxide, or a combination thereof. The box-nanocrystals and dendron-nanocrystals disclosed herein are examples of box-nanoparticles and dendron-nanoparticles, therefore the disclosure, reactions, and examples presented herein for box-nanocrystals and dendron-nanocrystals are exemplary for the more general applications to box-nanoparticles and dendron-nanoparticles.

In one aspect of this invention, the nanocrystal core of the box-nanocrystal comprises a CdSe nanocrystal, a CdS nanocrystal, or a CdSe/CdS core/shell nanocrystal. Further, the nanocrystal core can comprise a semiconductor, a magnetic material or compound (including ferromagnetic, ferrimagnetic, paramagnetic, super-paramagnetic, piezoelectric, piezomagnetic, or antimagnetic materials or compounds), a catalyst, an antibial, or materials with other chemical and physical properties. Further examples include, but are not limited to, an organic dye or a bio-active species. The box-nanocrystal and the nanocrystal core of this invention are characterized by an average diameter of typically less than about 100 nanometers.

One feature of this invention is its versatility. Thus, the nanometer-sized solid core of this invention can comprise a range of inorganic or organic compounds and substances, including but not limited to: 1) a metal oxide of varying topologies; 2) a metal-"non-oxide" element composition such as a metal boride, carbide, silicide, nitride, phosphide, arsenide, sulfide, selenide, telluride, halide (fluoride, chloride, bromide, or iodide), and the like; 3) a complex inorganic substance in which more than one metal is combined with an element, for example a bimetallic sulfide or a "mixed oxide" compound such as $BaTiO_3$ or $YMnO_3$; 4) a complex inorganic substance in which a metal is combined with more than one other element, for example, a metal oxycarbide; 5) a metal; 6) other binary or ternary compounds that combine non-metals with non-metals, such as boron nitride, or combine metals and metals, such as a bimetallic alloy; 7) an elemental non-metal such as silicon; 8) an organic compounds such as organic dyes or drug molecules; or 9) combinations or mixtures thereof.

Generally, the box-nanocrystal of this invention comprises cross-linkable dendron ligands that themselves comprise cross-linkable alkene, amine, hydroxyl, ester, halide, ketone, aldehyde, or other common functional groups prior to cross-linking. Typically, the box-nanocrystal of this invention comprises dendron ligands selected from generation 2 (G2), generation 3 (G3), generation 4 (G4), or generation 5 (G5) dendrons, wherein each dendron ligand is functionalized with one, two, three, four, or more binding sites for coordinating to the nanocrystal. In one aspect, the dendron ligands are selected from G3-(hydroxamide)-$CH=CH_2$, G3-(carboxylic)-$CH=CH_2$, G2-(amine)-ester, G3-(thiol)-$CH=CH_2$, G3-(diamine)-OH, G3-(thiol)-OH, G3-(dicarboxylic)-OH/PEG, or G4-(dicaboxylic)-$CH=CH_2$/PEG, prior to cross-linking. When the cross-linkable dendron ligands comprise alkene groups, these alkene groups may be substantially cross-linked by a ring-closure metathesis reaction.

Another aspect of this invention is a nanometer-sized particle, comprising a nanometer-sized solid core usually in the size range of about 1 nm and about 100 nm and a plurality of cross-linkable dendron ligands coordinated to the nanometer-sized inorganic core. In one aspect, the nanometer-sized solid core comprises a nanocrystal.

Another aspect of this invention is the dendron box itself, comprising a plurality of dendron ligands that have been substantially cross-linked, wherein the dendron box has an average inner diameter between about 1 nm and about 100 nanometers, and wherein the nanometer-sized inorganic core has been removed. Thus, this invention further encompasses a method of forming a dendron box comprising contacting a nanocrystal with a plurality of cross-linkable dendron ligands to form a dendron-coated nanocrystal (also called a "dendron nanocrystal"), cross-linking the dendron ligands to form a box-nanocrystal, and removing the nanocrystal from the box-nanocrystal to form the dendron box. Useful cross-linkable dendron ligands include, but are not limited to, G3-(hydroxamide)-CH=$CH_2$, G3-(carboxylic)-CH=$CH_2$, G2-(amine)-ester, G3-(thiol)-CH=$CH_2$, G3-(diamine)-OH, G3-(thiol)-OH, G3-(dicarboxylic)-OH/PEG, and G4-(dicaboxylic)-CH=$CH_2$/PEG. This invention also encompasses the removal of the nanocrystal from the box-nanocrystal by oxidation, acid treatment, thermolysis, and other chemical and photochemical etching techniques.

Another aspect of the present invention is a method of stabilizing a nanocrystal comprising contacting the nanocrystal with a plurality of cross-linkable dendron ligands to form a dendron-nanocrystal, and cross-linking the dendron ligands to form a box nanocrystal. Typically, the nanocrystal is a semiconductor nanocrystal, or is selected from CdS, CdSe, or CdSe/CdS core/shell nanocrystals, but this method of stabilization is also applicable to a number of materials that are not semiconductors. Also typically, the cross-linkable dendron ligands of this method comprise a thiol anchoring group and a plurality of cross-linkable alkene groups. Usually, the cross-linking of the alkene groups is effected by a ring-closing metathesis reaction, to cross-link substantially all the dendron ligands in the dendron-nanocrystal to form the box-nanocrystal.

Thus, in one aspect of this invention, in order to reach the desired global cross-linking, a "Generation 3" (G3) dendron with thiol anchoring group, and eight carbon-carbon double bonds as terminal groups was employed as the surface ligand. The relatively enhanced chemical stability of the dendron ligand-coated nanocrystals (dendron-nanocrystals) enabled the nanocrystal/ligand complexes to readily survive the cross-linking reaction and related purification procedures. Further, the multiple double bonds of each dendron ligand made it possible to obtain global cross-linking of substantially all the dendron ligands on the surface of each nanocrystal to form a "dendron box" around each nanocrystal, termed a "box-nanocrystal". Various methods were also developed that allowed the removal of the nanocrystal from the dendron-box, in which the cross-linked ligands remained intact and provided a useful capsule for a variety of molecular scale host-guest applications.

In one aspect, the present invention addresses the current limitations in nanocrystal stability by creating stable nanocrystal-ligand complexes by providing a globally cross-linked ligand monolayer for each nanocrystal. Through such cross-linking, the ligands around each nanocrystal form a ligand box. For simplicity, the resulting cross-linked nanocrystal-ligand complex is called a box-nanocrystal. As disclosed herein, this method is very versatile and is applicable to synthesizing and stabilizing a range of inorganic nanocrystals with different compositions, including but not limited to, metals, oxides, and chalcogenides.

Organic dendron ligands with functionalized terminal groups, especially terminal groups that can be cross-linked (referred to as cross-linkable dendrons), are particularly suited for the global cross-linking process if a large number of the terminal groups of each dendron are available for cross-linking. This feature affords a high probability that a dendron ligand will be cross-linked with its neighboring ligands in the ligand monomer of a given nanocrystal, thereby providing the desired stability to the box-nanocrystal. For example, a G3 dendron can have at least 8 terminal functional groups, although a global cross-linking of all ligands around each nanocrystal likely requires only two to three cross-linking sites.

While not intending to be bound by this statement, because dendrons are molecules with defined structures, all cross-linking sites could be readily designed at a close proximity to each other, which was thought to make the cross-linking reactions occur in a high yield. Further, the dendron ligands of this invention are typically characterized by flexible dendron chains, which is thought to allow significant intermolecular (that is, interdendron) chain tangling, a feature which should further assist intermolecular cross-linking. To enhance the bonding between nanocrystals and the dendron ligands, bidentate and multidentate binding sites may be designed at the focal point of the dendron ligands.

Different types of cross-linking strategies are suited for the global cross-linking reactions of all dendron ligands around each nanocrystal of this invention. Typically, maximum box-nanocrystal stability is achieved when a cross-linking reaction affords a substantially global cross-linking reaction. The formation of the dendron box around each nanocrystal to form a box-nanocrystal was confirmed by NMR, IR, TEM, and mass spectroscopy. The superior chemical, photochemical and thermal stability of the resulting box-nanocrystals were quantitatively or semi-quantitatively examined.

The resulting stable nanocrystals should be immediately applicable to many technical applications of nanocrystals, including but not limited to, LEDs, solid state lasers, biological labeling, MRI, drug delivery using magnetic nanocrystals, and the like. Further, cross-linked nanocrystal-ligand complexes (box-nanocrystals) are also of interest for many fundamental studies, such as measurement of the size-dependent melting point of nanocrystals and studies on the size-specific reactivity of nanocrystals.

In addition, empty dendron boxes without the enclosed nanocrystal, formed by the dissolution of inorganic nanocrystals in an etching solution, are also provided by the present invention. These empty dendron boxes represent a new class of nanometer sized polymer capsules, which are nearly monodisperse, soluble, stable, and which possess a very thin periphery. These empty dendron boxes find utility in may ways, including as molecular sieves, in host-guest applications, as encapsulating agents for drug delivery, molecular imprinting, and the like.

Accordingly, it is one aspect of the present invention to provide new cross-linked nanocrystal-ligand structures (box-nanocrystals) to impart and maintain greater stability to the nanocrystal-ligand complex.

It is another aspect of this invention to develop new processing methods that will prevent dissociation of organic ligands from the inorganic nanocrystal core, and avoid the thermal instability, chemical oxidation, etching, photochemical instability, or dissolution of the inorganic core itself.

Another aspect of this invention is the enhancement of the stability of the ligand monolayer by substantially cross-linking all the surface ligands of each nanocrystal through methods that include, but are not limited to, ring-closing metathesis (or RCM) reactions, to form cross-linked nanocrystal-ligand structures.

It is another aspect of this invention to develop and utilize a dendrimer-bridging strategy for the formation of box-nanocrystals.

Another aspect of this invention is the use of the improved stability of dendron-coated nanocrystals (referred to as dendron-nanocrystals) to provided the needed stability to the nanocrystal-ligand complex, such that it can remain intact during the cross-linking reaction of the dendron ligands and related purification procedures.

Still another aspect of this invention is the global cross-linking of substantially all the dendron ligands on the surface of each nanocrystal to form a dendron box around each nanocrystal, that is, to provide a box-nanocrystal.

Yet a further aspect of this invention is the formation of an empty dendron box, without the enclosed nanocrystal, which can be used as nanometer-sized polymer capsules, new types of molecular sieves, in host-guest applications, and the like.

Another aspect of this invention is the conjugation of chemical and biochemical functional species, including but not limited to DNA, RNA, peptides, polypeptides, nucleic acids, amino acids, sugars, proteins, antibodies, and the like, onto the surface of box-nanocrystals.

Yet another aspect of this invention is the detection of bio-active species using the stable box-nanocrystals, wherein binding of the bio-active species to the biomedical functional species attached onto the surface of box-nanocrsytals occurs specifically. Another aspect of this invention is the detection of avidin by this method.

These and other features, aspects, objects, and advantages of the present invention will become apparent after a review of the following detailed description of the disclosed embodiments and appended claims, in conjunction with the drawings described as follows.

biotinated box-nanocrystals plus plain PBS buffer; and (2) amine box-nanocrystals plus Avidin in PBS buffer.

Figure 17:
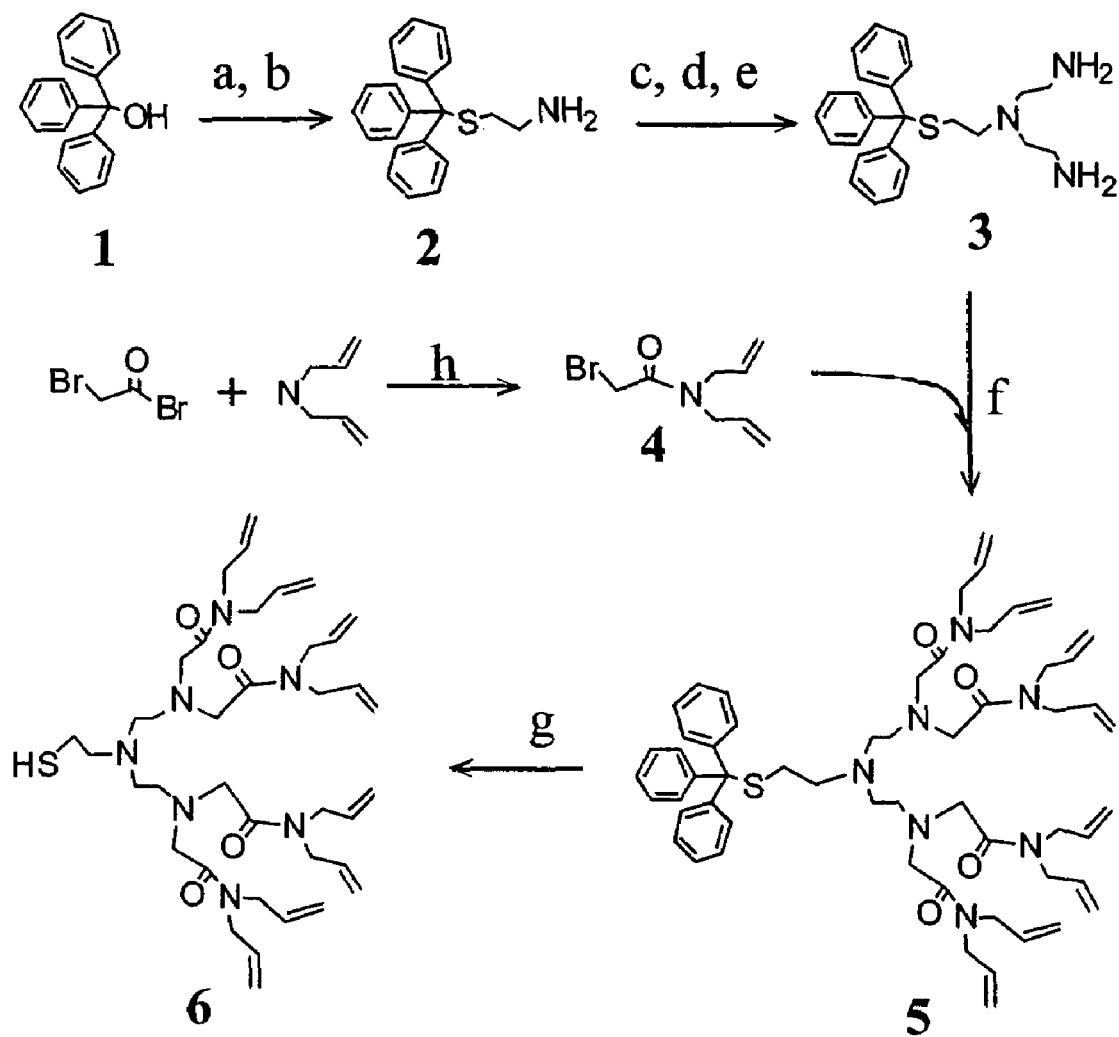

FIG. 17 provides a reaction scheme for the synthesis of dendron ligands, wherein the reagents, conditions, and yields are disclosed in Example 1.

Figure 18:
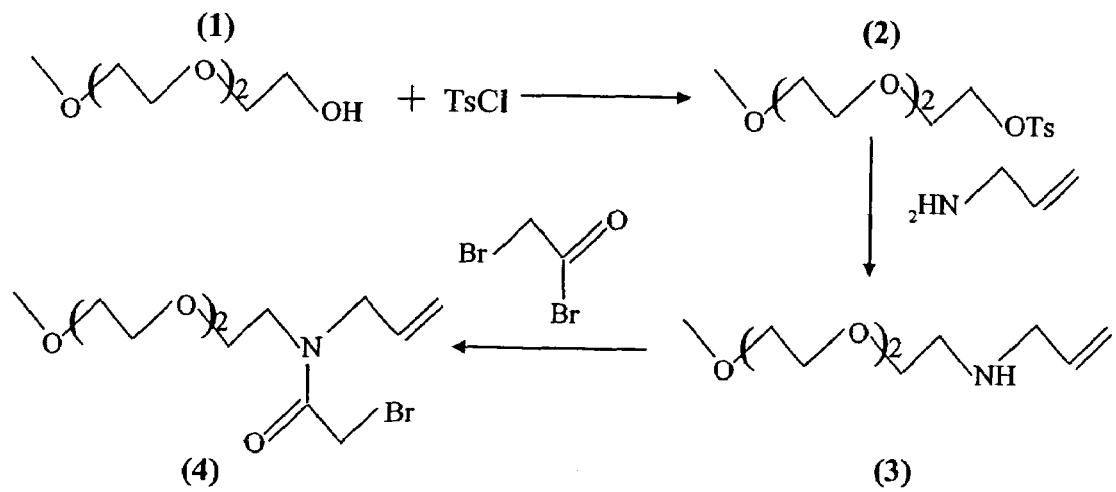
Figure 18:
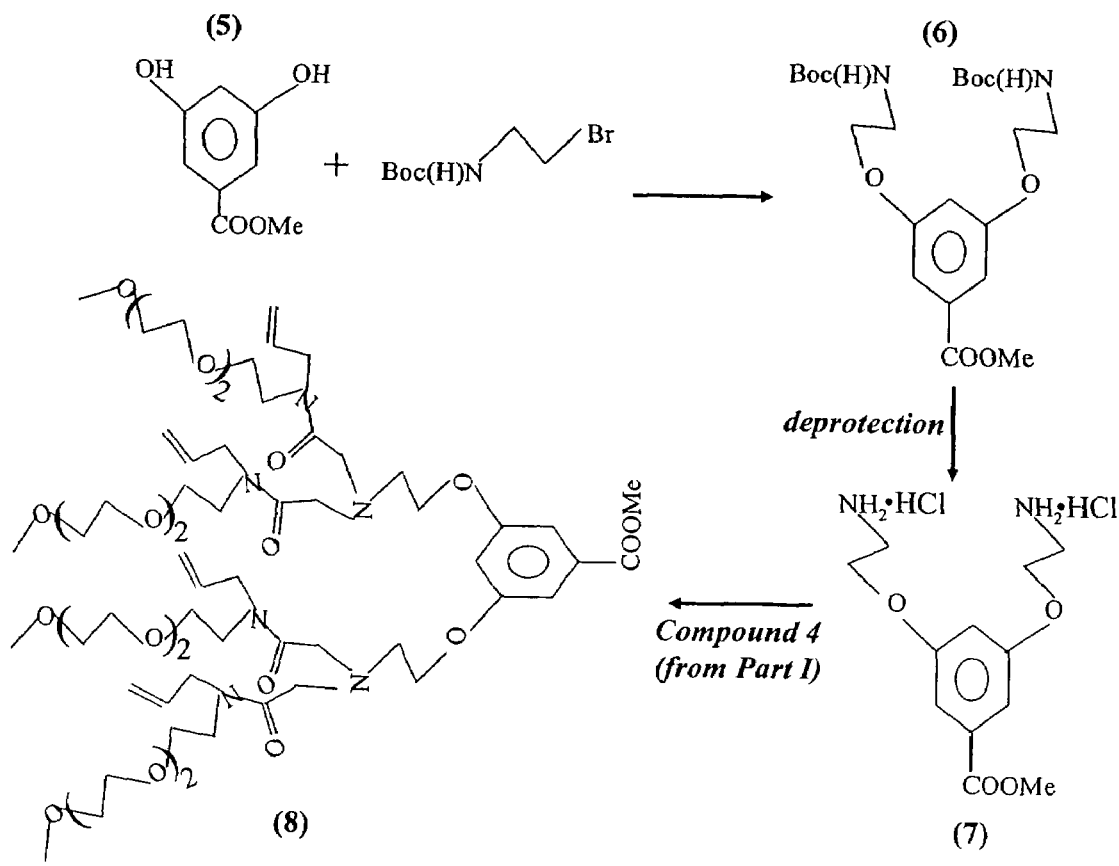

FIG. 18 provides reaction schemes for the synthesis of an asymmetric dendron ligand, namely compound 8, which is applicable to this particular compound and its analogs and derivatives.

Figure 19:
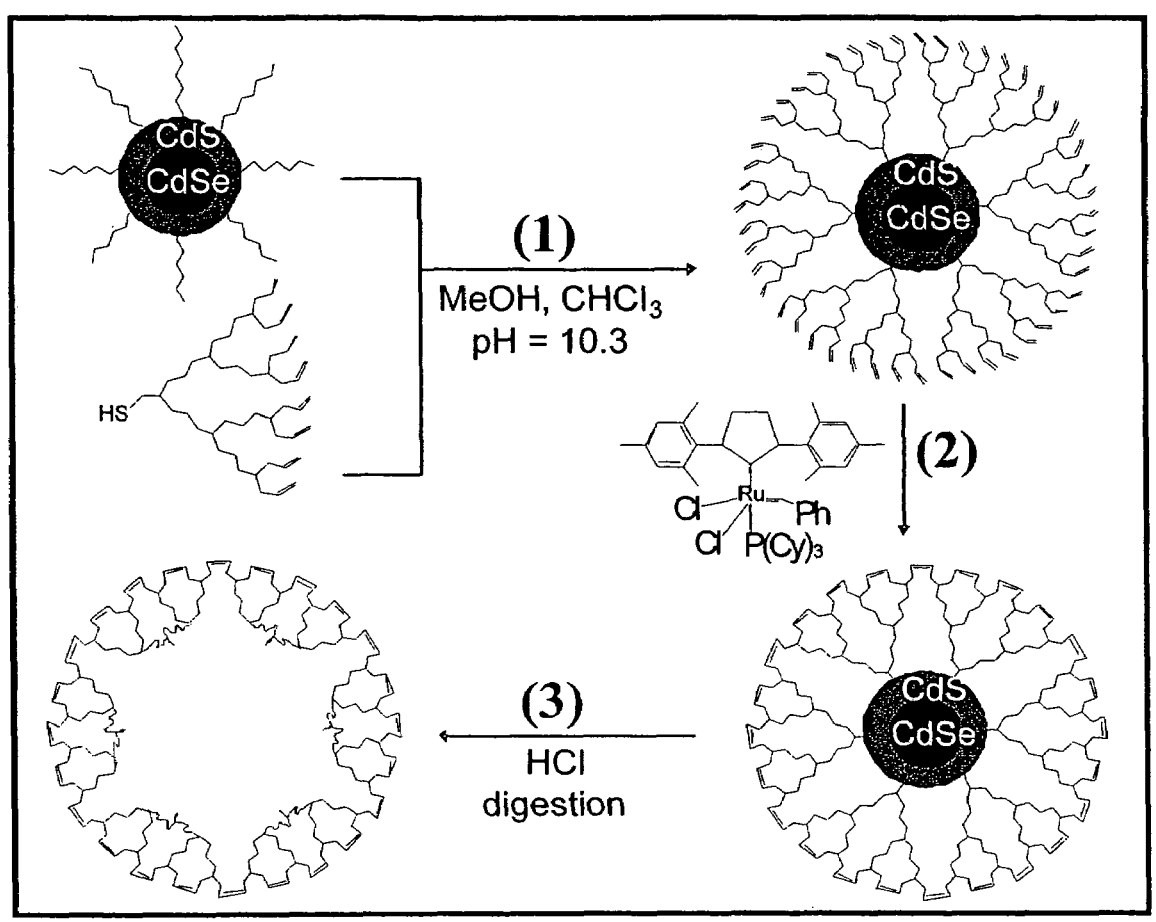

FIG. 19 illustrates a reaction scheme for cross-linking the terminal allyl groups of the dendron-nanocrystals to form box-nanocrystals using Grubbs' ruthenium alkylidene catalyst.

Figure 20:
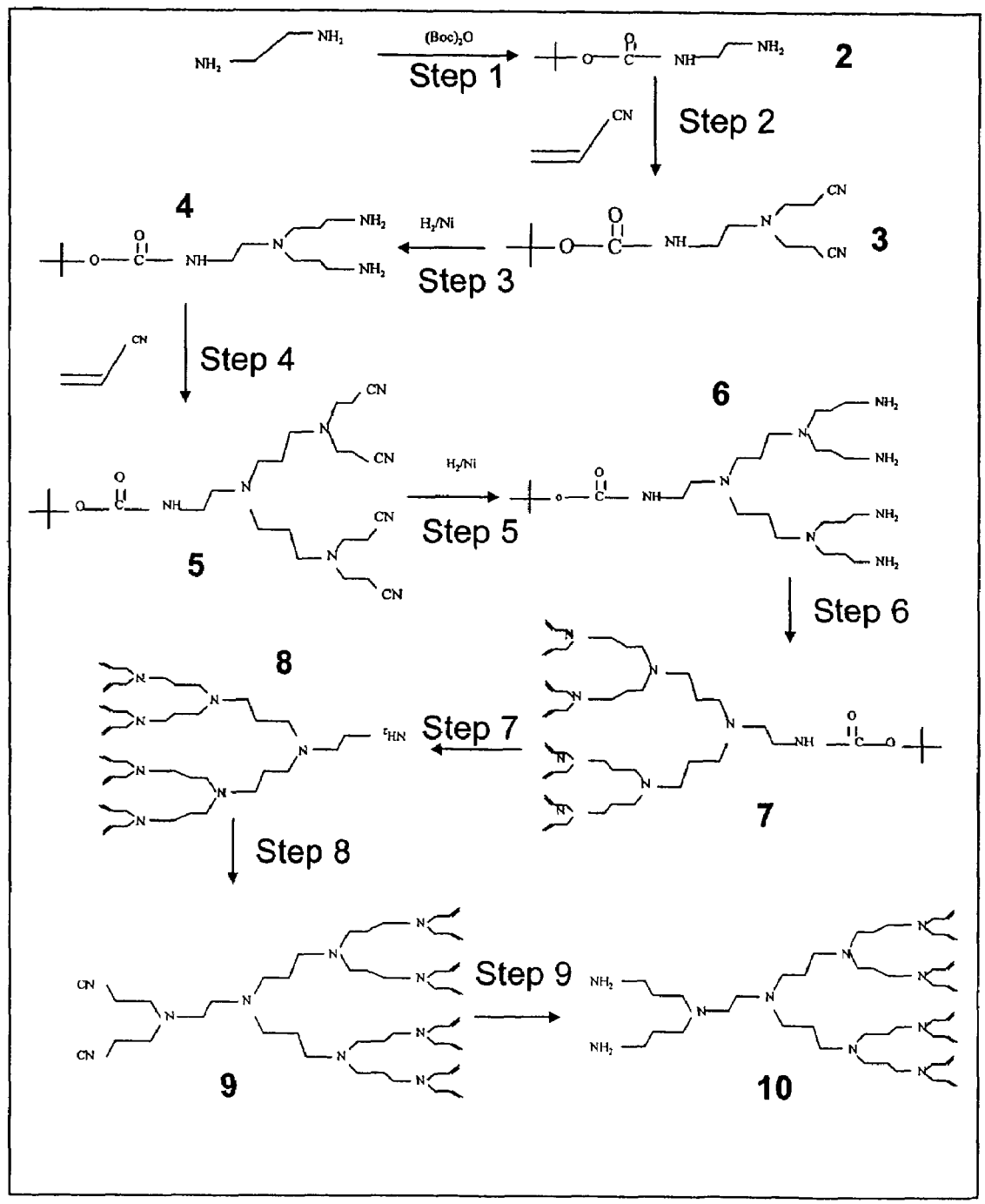

FIG. 20 illustrates the synthetic procedure for a bidentate dendron ligand.

DETAILED DESCRIPTION OF THE INVENTION

The present invention provides a class of highly stable nanocrystal-ligand complexes, referred to as box-nanocrystals, and methods and processes for kinetically stabilizing nanocrystal complexes. The enhanced stability of the ligand monolayer was achieved by the substantially global cross-linking of all the dendron ligands on the surface of each nanocrystal to form a dendron box around each nanocrystal. The cross-linking reactions may be achieved by a variety of methods including, but not limited to, ring-closing metathesis reactions, dendrimer-bridging, and complex formation. The present invention further provides for the formation of an empty dendron box without the enclosed nanocrystal, which can be used as nanometer-sized polymer capsules for a variety of host-guest type complexes and applications.

Design and Synthesis of Dendron Ligands for Box-Nanocrystals

The formation of box-nanocrystals typically employs dendron or other branched ligands having a certain number of cross-linking points for the global cross-linking reactions involving all ligands around each nanocrystal. The backbone and periphery of the dendrons should be flexible to afford significant intermolecular chain tangling and reduce steric factor for cross-linking reactions to occur.

The focal point of the dendrons, that is an initial molecular branching point, was chosen as the bonding point to the surface of nanocrystals. To enhance the overall bond strength between dendron ligands and the nanocrystal, bidentate and multidentate ligands were also considered. For nanocrystals with different compositions, different bonding or coordination sites on the dendron ligands were typically selected. For example, nanocrystals comprising noble metals or most semiconductor materials typically coordinated with relatively soft ligand bonding sites, such as thiols, amines, phosphines, phosphine oxides, carboxylic acid, phosphonic acids, phosphinic acids, and the like. Nanocrystals comprising transition metals or transition metal compounds typically bonded with ligand sites such as hydroxamate, sophonic, silicate, amines, phosphines, phosphine oxides, carboxylic acid, phosphonic acids, phosphinic acids, and the like. Nanocrystals of some elemental non-metals, such as silicon and germanium, typically bonded with ligands comprising alkene, halide, or hydroxyl groups, and the like. The binding sites for organic nanoparticles varied by the structure and surface of the nanoparticles. Various choices for dendron bonding or coordination sites used for other types of nanocrystal surface atoms or ions can be found in standard references on inorganic coordination chemistry and organic chemistry.

Figure 1:
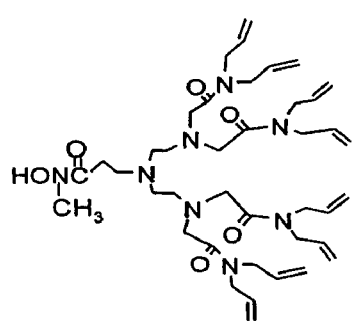
FIG. 1 provides several representative examples of cross-linkable dendron ligands used to stabilize nanocrystals and to prepare box-nanocrystals of the present invention.
Figure 1:
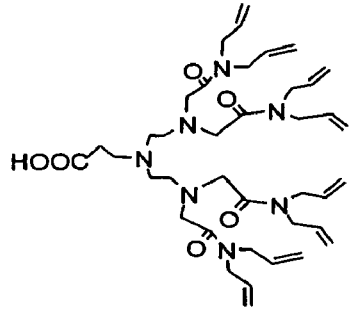
Figure 1:
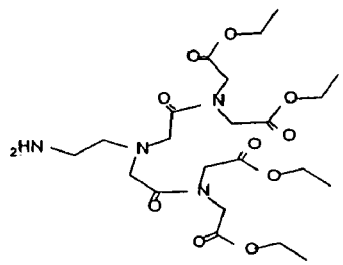
Figure 1:
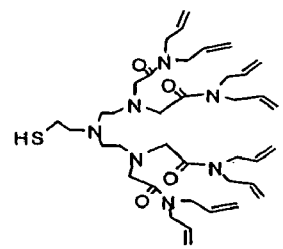
Figure 1:
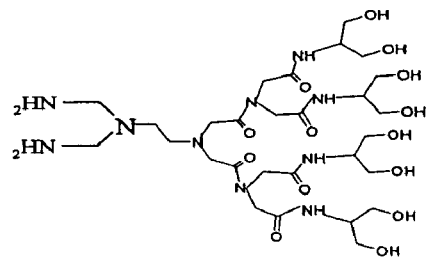
Figure 1:
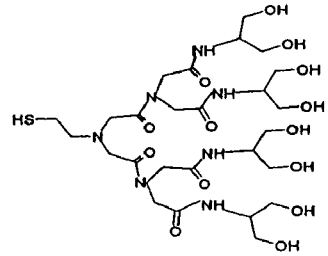
Figure 1:
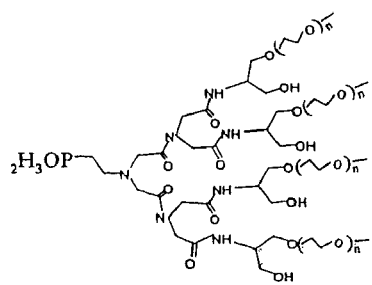
Figure 1:
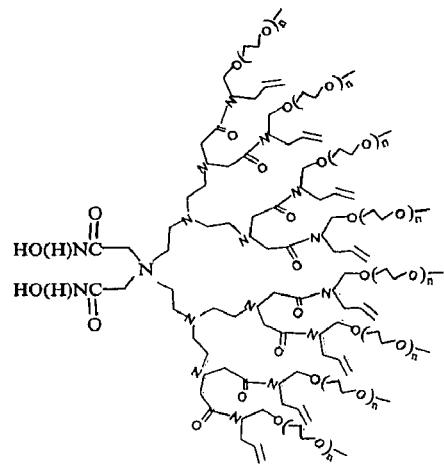

FIG. 1 and the Examples provides several representative examples of cross-linkable dendron ligands used to stabilize nanocrystals and to prepare box-nanocrystals of the present invention. The preparation and properties of these cross-linkable dendron ligands are found in the Examples provided herein, and in the publications or patents mentioned herein (for example, Guo, et al., Journal of the American Chemical Society, 2003, volume 125, page 3901-3909; Guo, et al., Chemistry of Materials, 2003, volume 15, page 3125-3133), each of which is hereby incorporated by reference in its entirety. For example, Example 16 provide the stepwise synthesis of a new dendron ligand of the present invention characterized by a bidentate binding site at the focal point of the dendron ligands.

FIG. 1 is not intended to be limiting, but rather provide illustrative examples of cross-linkable dendron ligands of this invention. For example, the backbone and terminal groups of the dendron ligands can be varied over a wide range of possible choices, as long as they are substantially resistant to the necessary chemical, biochemical, photochemical, thermal treatments, and the conditions typically required for processing the dendron-nanocrystals and box-nanocrystals.

Formation of Box-Nanocrystals via Ring-Closing-Metathesis (RCM) Reactions

Figure 2:
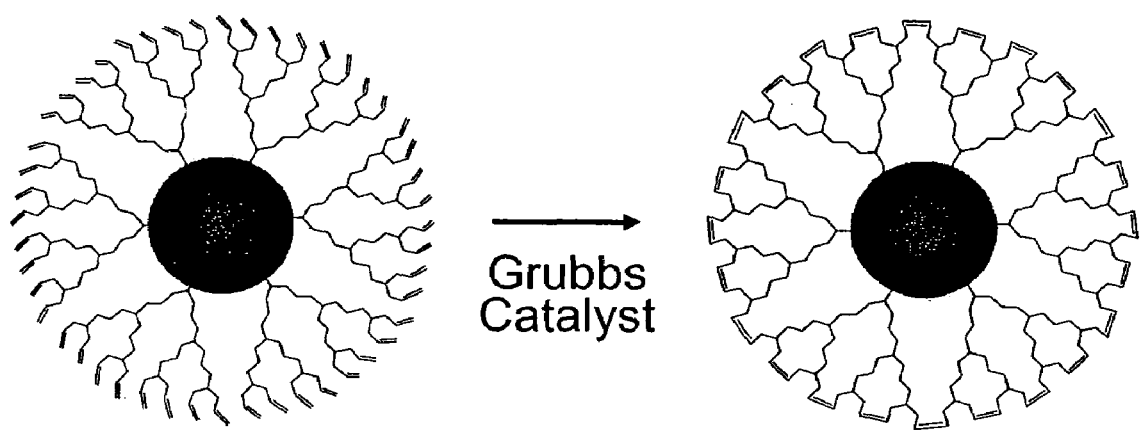
FIG. 2 illustrates a type of ring-closing metathesis (or RCM) reaction using the Grubbs catalyst, which is one method of cross-linking used to prepare box-nanocrystals of the present invention.

The ring-closing metathesis (RCM) reaction comprises one method of cross-linking the dendron ligands surrounding a nanocrystal to form box-nanocrystals. If the dendron ligand comprises terminal groups which are all or partially carbon-carbon double bonds, RCM reactions can readily occur using any ring-closing metathesis catalyst, including but not limited to the Grubbs catalyst. FIG. 2 illustrates a type of intraparticle ring-closing metathesis (or RCM) reaction to cross-link dendron ligands comprising C=C double bonds to prepare box-nanocrystals of the present invention. To avoid interparticle cross-linking, the reactions should be carried out with a relatively low particle concentration.

A typical RCM cross-linking process of this invention employs the second generation Grubbs' ruthenium catalyst as described in detail in Example 11. The catalyst (2 mol % per alkene group) was added to a solution of the dendron-nanocrystals. In calculating this concentration of alkene groups, the amount of ligands on the surface of CdSe/CdS core/shell nanocrystals was estimated by assuming a close packing of ligands on the surface of nanocrystals. The box-nanocrystals that were prepared were precipitated out of solution with an appropriate solvent, and separated by centrifugation and decantation. The reactions provided herein may be altered when the size and composition of the nanocrystals are different.

Formation of Box-Nanocrystals via Dendrimer-Bridging Reactions

Another method of cross-linking the dendron ligands surrounding a nanocrystal to form a box-nanocrystal is to globally cross-link these ligands using a second, linker molecule. Thus, the terminal functional groups of dendron ligands are selected such that they can be globally cross-linked using a linker molecule.

Dendrimers are closely related to the dendrons. However, unlike a dendron, a dendrimer does not have a focal point. In general, when two, three or four dendrons chemically linked to each other at their focal points, a dendrimer molecule is formed. Dendrimer molecules with flexible backbones worked extremely well as the linker species. Thus, while functionalized dendron ligands used to coordinate to and surround the nanocrystal core, dendrimer molecules with flexible backbones and functionalized with reaction-complimentary functional groups are used as the linkers by which to globally link the coordinated dendron ligands around the nanocrystal core. While not intending to be bound by this statement, it is believed that the bulky, flexible structure of the dendrimer facilitates this ease of cross-linking. When one functional groups of a multi-functional dendrimer reacts with one terminal group of a dendron ligand, the steric bulk of the dendrimer likely prevents access of another dendrimer molecule to the terminal functional groups on a neighboring dendron ligand. Thus, the functional groups of the other flexible branches on the same dendrimer have a greater chance to react with the terminal groups on the neighboring dendron ligand at the same nanocrystal core. As a result, global cross-linking is possible.

Figure 3:
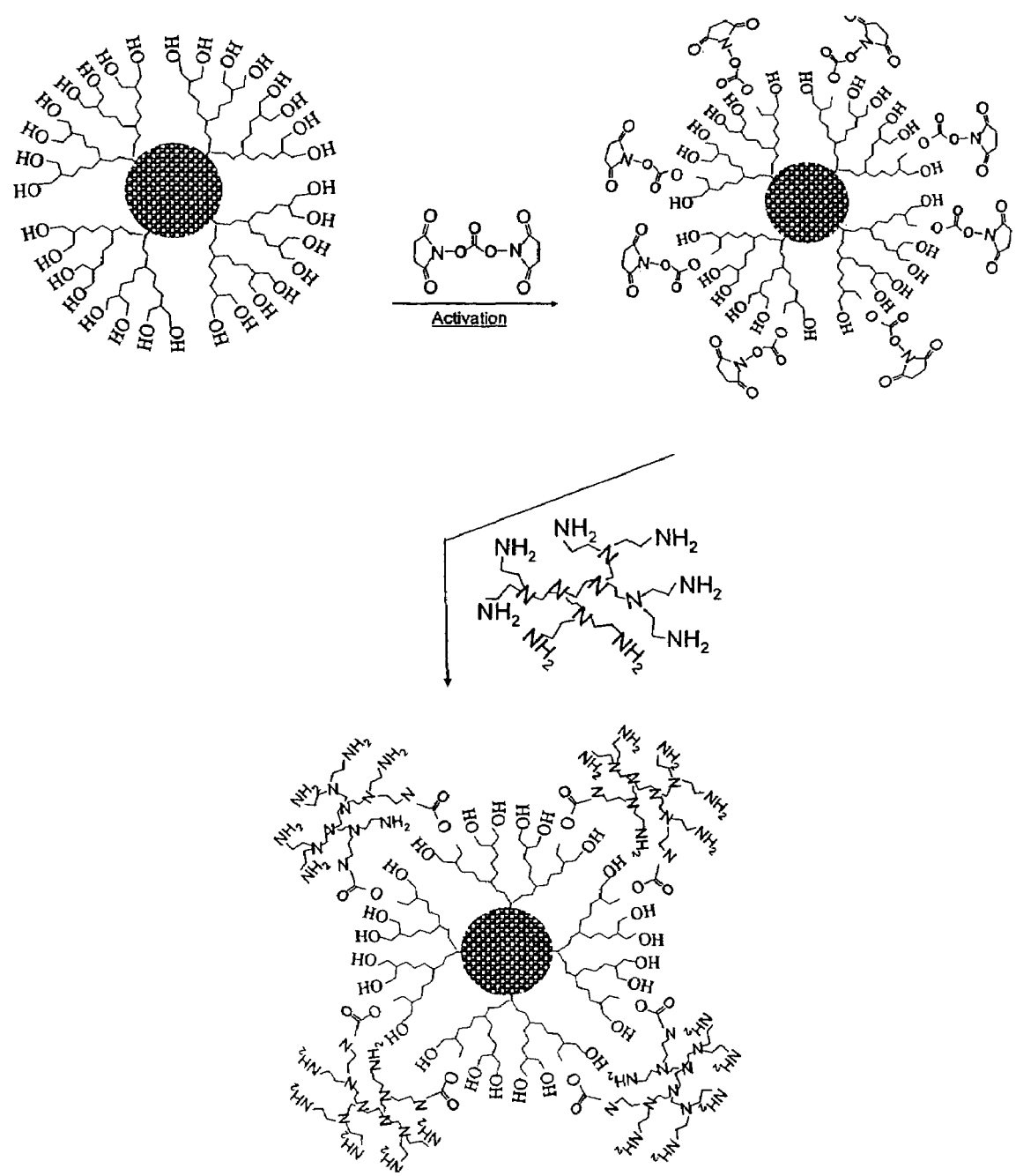
FIG. 3 illustrates the dendrimer-bridging method for the formation of box-nanocrystals. The cross-linking strategy shown in this figure provides global cross-linking of all dendron ligands on each nanocrystal and also functionalizes the nanocrystal with amine groups.

FIG. 3 illustrates the dendrimer-bridging method for the formation of box-nanocrystals, the details of which are provided in Example 12. The cross-linking strategy shown in this figure provides global cross-linking of all dendron ligands on each nanocrystal and also functionalizes the nanocrystal with amine groups. In this reaction, the homo-bifunctional cross linker, N,N-disuccinimidyl carbonate (DSC) and 4-(dimethylamino)pyridine (DMAP) were added to a solution of the G3-OH coated nanocrystals. The absorbance at the first exciton peak of the nanocrystals solution was observed to be 1.26. After the solution was stirred overnight, a portion of this solution was added to another solution containing the G2 dendrimer amine, the structure of which is shown in FIG. 3, to form the box-nanocrystal. The amine box-nanocrystal solutions were kept dispersible by maintaining the solution between pH=2 to pH=9. The reactions provided here may be altered when the size and composition of the nanocrystals are different.

Experimentation also revealed that small bifunctional or trifunctional linker molecules were typically not optimum for the formation of box-nanocrystals in this type of reaction, because these small multifunctional linkers usually have rigid molecular structures. These structural features typically result in the cross-linking reactions competing with mono-coupling events between the terminal functional groups and the small linker species, thereby resulting insufficient cross-linking.

Properties of the Box-Nanocrystals and Experimental Evidence for their Formation Various physical and chemical properties of the box-nanocrystals of this invention were observed in the course of characterizing these species by a variety of methods. Further, this experimental evidence demonstrated that the nanocrystal core remained intact in the box-nanocrystal, and that the cross-linking reaction did not result in degradation or loss of the dendron ligand sheath or casing from the nanocrystal core. For example, the key optical properties of the nanocrystals were verified to be substantially identical before and after the cross-linking process. Thus, the absorption and emission spectra of semiconductor nanocrystals did not change after the cross-linking.

Figure 4:
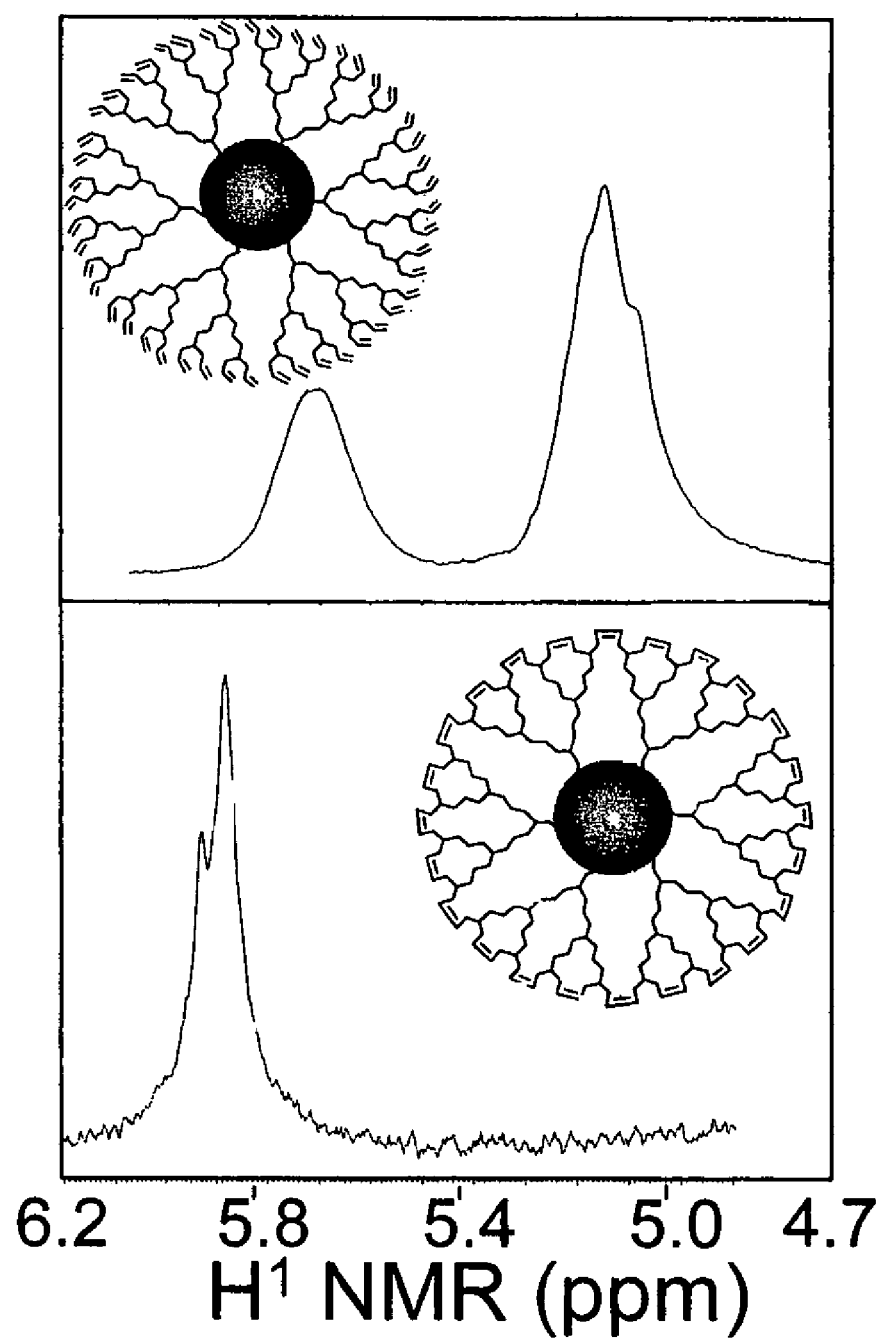
FIG. 4 provides $^1$H NMR spectra of a dendron-nanocrystal complex both before and after the ring-closing metathesis (RCM) cross-linking reaction, illustrating the substantially complete cross-linking reaction.

The completion of the cross-linking reactions was determined by NMR and IR spectroscopy by detecting certain fingerprint features of the complex. For example, as shown in FIG. 4, the $^1$H NMR spectra of a dendron-nanocrystal complex both before and after the ring-closing metathesis (RCM) cross-linking reaction clearly demonstrate that the RCM cross-linking reaction occurred quantitatively on the surface of nanocrystals.

Figure 5:
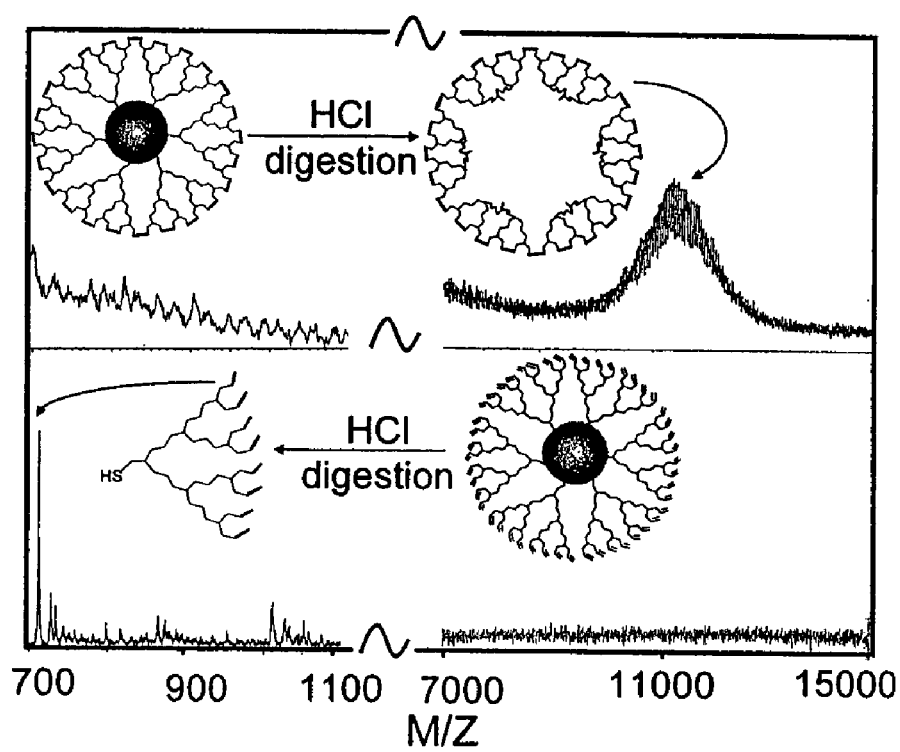
FIG. 5 provides mass spectra of the solutions obtained by digestion of CdSe dendron-nanocrystals before (bottom) and after (top) the cross-linking reaction, illustrating the intact, cross-linked, nanometer-sized polymer capsule that is obtained from digestion of the box-nanocrystal.

In addition, strong evidence of the "global" nature of the cross-linking of substantially all the dendron ligands of a given nanocrystal was provided by mass spectrometry measurements, using the clear solution obtained by the HCl digestion, as shown in FIG. 5. Thus, FIG. 5 provides mass spectra of the solutions obtained by digestion of CdSe dendron-nanocrystals before (bottom) and after (top) the cross-linking reaction, illustrating the intact, cross-linked, nanometer-sized polymer capsule that is obtained from digestion of the box-nanocrystal. Before cross-linking, only the dendron ligands in the digestion solution were detected by mass spectrometry. However, after cross-linking, a distinguishable peak with a very high molecular mass (m/z) dominated the spectrum. Typically, the related mass of the peak observed after cross-linking corresponded to about 15 to 50 dendron units with a full width at half maximum (FWHM) of 2 to 5 dendron units. This number is in good agreement with the values measured by the gravimetric method before digestion, as described in the examples.

A measure of the average number of the dendron units on the surface of each box-nanocrystal before HCl digestion was obtained as follows. Nanocrystals after the cross-linking process were carefully purified and the purity was examined by $^1$H NMR spectroscopy. Typically, if any free small molecules existed in the solution, very sharp and intense $^1$H NMR signals would be detected. A known amount of the purified nanocrystals in the form of fine powder was weighed to determine the total mass of the nanocrystal-ligand complex, and then, those nanocrystals were dispersed in a known-volume solvent. The total number of inorganic nanocrystals in the solution was determined by the absorbance of the solution and the extinction coefficient of the nanocrystals. The size of the nanocrystal core was determined by the first peak of the absorption spectrum or transmission electron microscopy measurements. With this information in hand, the average number of the dendron units per nanocrystal could be easily calculated, through standard chemical methods.

This agreement between the gravimetric measurements and the mass spectrometry measurements on the number of dendron units before and after the HCl digestion revealed two important features. First, the mass peak of the empty boxes should be the signal from the singly-charged ions. Second, the cross-linking between nanoparticles was insignificant. While not intending to be bound by this statement, this lack of significant inter-particle cross-linking probably arises from an entropic effect, given the closely packed nature of the double bonds at the outer surface of the ligand monolayer on each nanocrystal, as well as the relatively low molar concentration of the nanocrystals.

Figure 6:
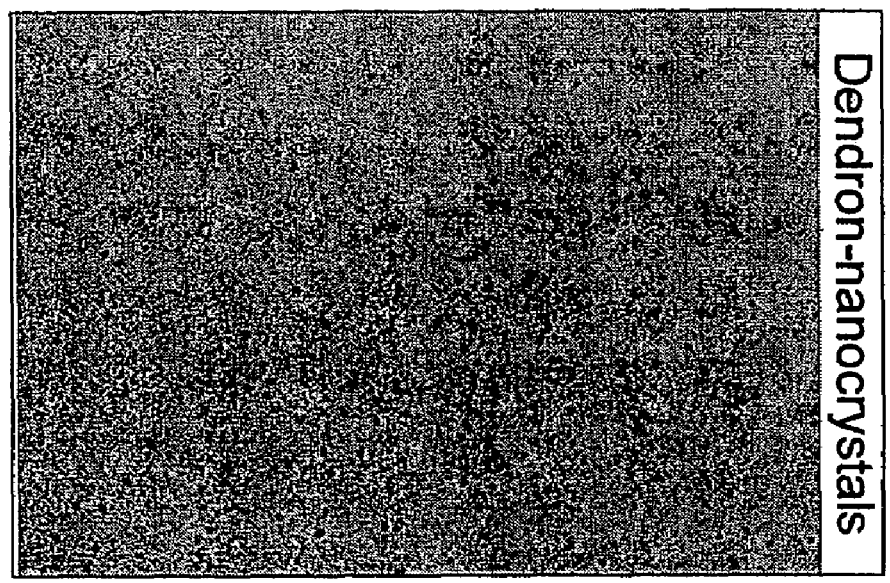
FIG. 6 provides TEM (transmission electron microscopy) images of 3.5 nm CdSe nanocrystals before (dendron-nanocrystals) and after (amine box-nanocrystals) the amine-dendrimer-bridging cross-linking reaction. The TEM image after cross-linking is substantially identical to the TEM image before cross-linking. Thus, most of the nanoparticles are well-separated from any nearest neighbor by a distance significantly larger than that expected had inter-particle coupling been a significant event.
Figure 6:
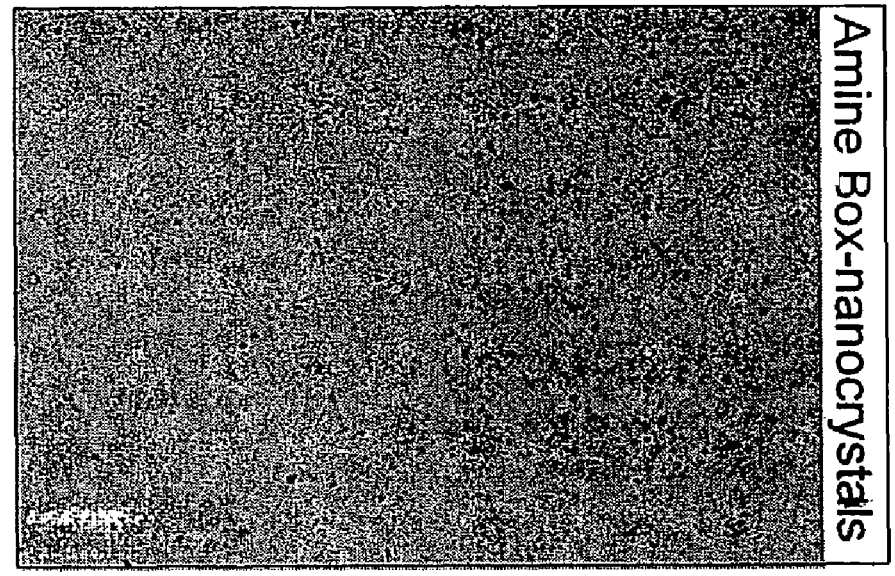

Transmission electron microscopy (TEM) measurements also provided strong evidence that inter-particle cross-linking was insignificant. FIG. 6 provides TEM (transmission electron microscopy) images of 3.5 nm CdSe nanocrystals before (dendron-nanocrystals) and after (amine box-nanocrystals) the amine-dendrimer-bridging cross-linking reaction. One example of this cross-linking reaction is illustrated in FIG. 3. As FIG. 6 illustrates, the TEM image after cross-linking is substantially identical to the TEM image before cross-linking. Thus, most of the nanoparticles are well-separated from any nearest neighbor by a distance significantly larger than that expected had inter-particle coupling been a significant event.

Further, the formation of box-nanocrystals often altered the solubility of the nanocrystals in a variety of solvents in ways consistent with the expected structure resulting from intra-particle cross-linking. For example, carbon-carbon double bond-terminated box-nanocrystals formed by RCM reactions often became only soluble in aromatic solvents or polar organic solvents, such as benzene, DMSO, and DMF. The solubility of the box-nanocrystals was considered to be consistent with the resulting structures of the cross-ring metathesis.

Stability of Box-Nanocrystals Under Severe Chemical Conditions

The present invention also provides new compositions and methods involving ligands to enhance the chemical, photochemical and thermal stability of colloidal nanocrystals. Examples of how CdSe box-nanocrystals exhibit superior stability against chemical treatments are seen in both their stability in the presence of strongly acidic solutions and in the presence of strongly oxidizing environment, as illustrated in FIG. 7.

Figure 7:
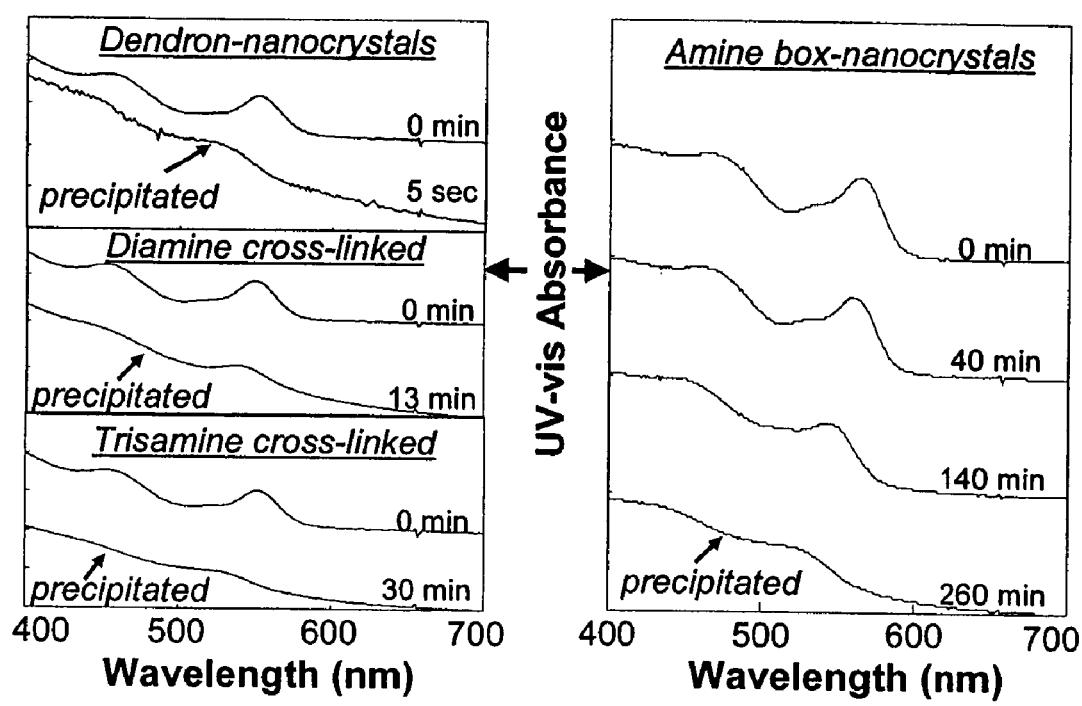
FIG. 7 provides UV-Vis spectra of various CdSe dendron-nanocrystals and box-nanocrystals, illustrating nanocrystal stability with different types of ligand shells against acid etching. Top-Left. Upon exposure to a strong acid, HCl (pH=1.5 and $[H]^+$=0.03 M), CdSe dendron-nanocrystals decomposed immediately, the inorganic nanocrystals precipitated out of the solution, and the first absorption peak of the solid residual was drastically shifted to blue, indicating a significant shrinkage of the inorganic nanocrystals. The stability against HCl etching of CdSe nanocrystals cross-linked using small molecular linkers, namely ethylenediamine (Middle-Left) and tris(2-aminoethyl)amine (Bottom-Left) are also illustrated. Right. The stability against HCl etching of the corresponding CdSe amine-box-nanocrystals prepared through the dendrimer-bridging method is illustrated by the substantially zero blue-shift of the first absorption peak of the CdSe box-nanocrystals within 40 minutes of the acid etching reaction.

FIG. 7 provides UV-Vis spectra of various CdSe dendron-nanocrystals and box-nanocrystals, illustrating nanocrystal stability with different types of ligand shells against acid etching. FIG. 7 (left side) reveals that, upon exposure to a strong acid, HCl (pH=1.5 and $[H]^+=0.03$ M), the CdSe dendron-nanocrystals decomposed immediately and the inorganic nanocrystals precipitated out of the solution (FIG. 7, top left). The first absorption peak of the solid residual was drastically shifted to blue, indicating a significant shrinkage of the inorganic nanocrystals. However, it took about 4 hours for the corresponding CdSe box-nanocrystals prepared through the dendrimer-bridging method to precipitate (FIG. 7, right). As also illustrated by the spectra on the right side of FIG. 7, the stability of the amine-box-nanocrystals of this invention is illustrated by the substantially no blue-shift of the first absorption peak of the CdSe box-nanocrystals within 40 minutes of the acid etching reaction.

FIG. 7 also demonstrates the stability against HCl etching of the CdSe nanocrystals cross-linked using small molecular linkers, namely ethylenediamine (middle-left) and tris(2-aminoethyl)amine (bottom-left). Although significant improvement in the stability against HCl etching was evidenced by the cross-linking using the small linkers, box-nanocrystals (right) which are the products of the global cross-linking process, showed superior stability in comparison among all the nanocrystals shown in FIG. 7.

Figure 8:
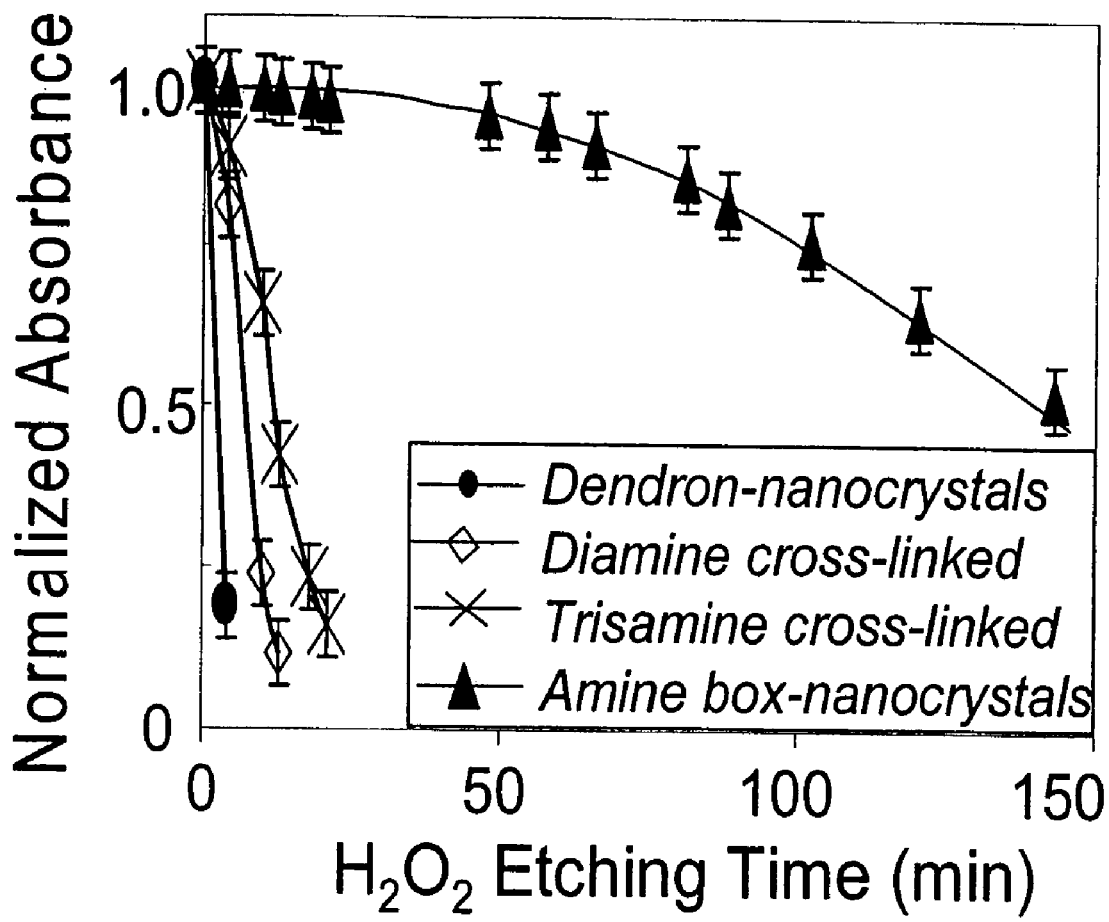
FIG. 8 plots the temporal evolution of the absorbance at the first absorption peak of the nanocrystals upon chemical oxidation using hydrogen peroxide. In each sample, measurements were stopped at the precipitation point of each sample.

A strong oxidant, $H_2O_2$ (0.15 mol/L), was found to etch CdSe, as well as many other semiconductor nanocrystals. The dendron-nanocrystals were much less stable than the corresponding box-nanocrystals when they were exposed to $H_2O_2$. FIG. 8 illustrates the relative stability of the various nanocrystals by plotting the temporal evolution of the absorbance at the first absorption peak of the nanocrystals upon chemical oxidation using hydrogen peroxide. In each sample, measurements were stopped at the precipitation point of each sample. Thus, for CdSe dendron-nanocrystals, oxidation of the nanocrystals was immediately detected and the inorganic nanocrystals precipitated after a few minutes in the $H_2O_2$ solution. The CdSe box-nanocrystals however were about 100 times more stable than the corresponding dendron-nanocrystals although slow oxidation of the inorganic core was also observed. Precipitation of the nanocrystals occurred after the reaction proceeded for about 150 minutes in the case of the CdSe box-nanocrystals prepared through the amine-dendrimer-bridging strategy. Again, local cross-linking through the small linkers improved the stability of the nanocrystals although the stability of the small linker nanocrystals was significantly less than that of the box-nanocrystals.

Further, the CdSe/CdS core/shell nanocrystals were generally more stable than the corresponding plain core nanocrystals. In particular, the core/shell box-nanocrystals did not show any detectable change upon exposure to $H_2O_2$ at a similar concentration for at least several hours. Further, the chemical stability of box-nanocrystals and their precursors, dendron ligands coated nanocrystals (dendron-nanocrystals), is a function of the chemical composition of the inorganic nanocrystals. For instance, box-nanocrystals with a metal oxide nanocrystal core were found to be generally more stable than the metal chalcogenide nanocrystals.

Thermal Stability of Box Nanocrystals

Thermal stability of the nanocrystals was examined by sintering the purified nanocrystal powder at 100° C. for a various amounts of time under vacuum. Except for the sintering process, the purification, storage and other processes were all handled in air under ambient conditions. It has been observed that nanocrystals coated with typical commercial ligands such as mercaptoacetic acid often do not survive the purification process, which may include repeated steps of dissolution, precipitation, and air-drying. In contrast, the dendron-nanocrystals of this invention survive these routine treatments without having their solubility substantially effected.

Figure 9:
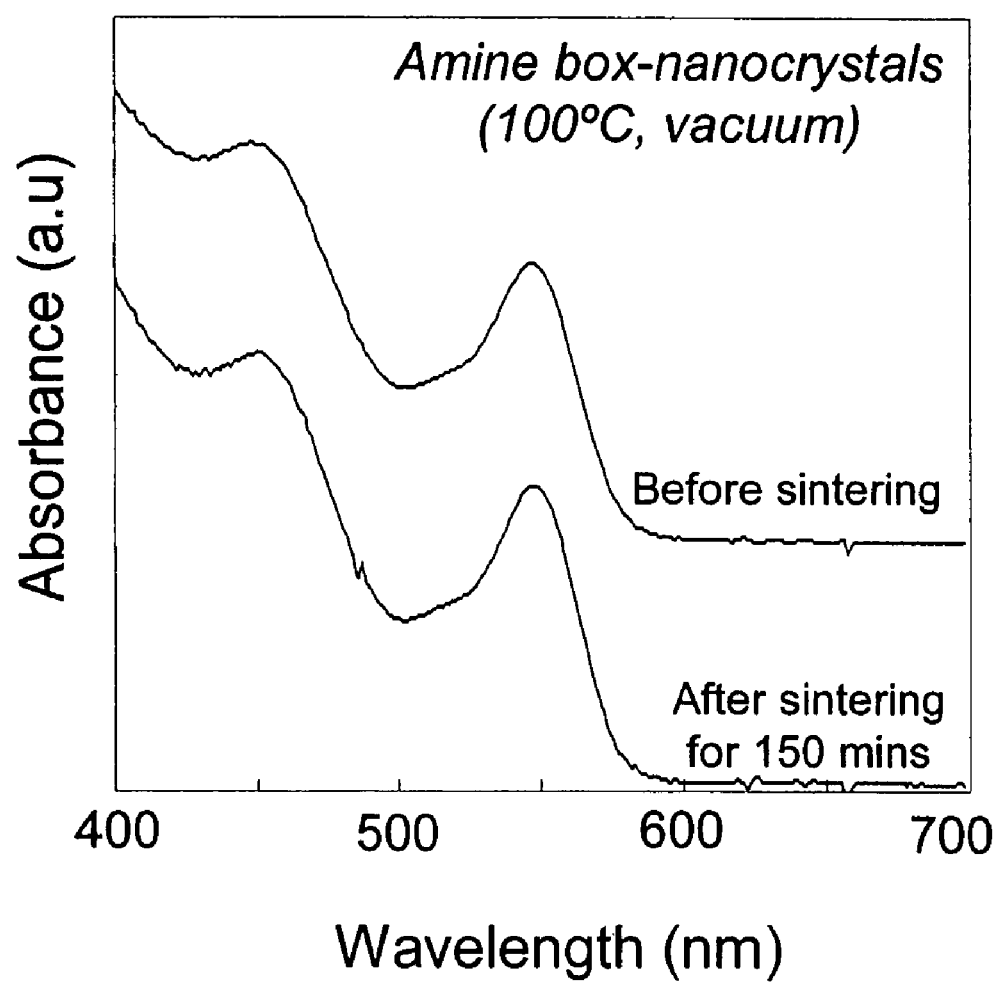
FIG. 9 plots the UV-Vis spectra of CdSe box-nanocrystals before and after sintering at 100° C. for 150 minutes, illustrating the stability of these box-nanocrystals of this invention.

The CdSe dendron-nanocrystals did not survive the harsh heating treatment (100° C., vacuum), although they could be dried under vacuum at room temperature. After sintering, the CdSe dendron-nanocrystals became insoluble in typical solvents. By comparison, the solubility of the CdSe box-nanocrystals was well-maintained after this sintering process, and no change in the optical properties of the nanocrystals was detected. As shown in FIG. 9, the UV-Vis spectra of the CdSe box-nanocrystals did not show any change before and after sintering at 100° C. for 150 minutes.

The excellent thermal stability of box-nanocrystals suggests that the known, irreversible aggregation of colloidal nanocrystals in solid state can be efficiently halted by "sealing" each nanocrystal inside a dendron box by the process of cross-linking the dendron ligands. It is believed that cross-linking both isolates the nanocrystals from each other and makes it very difficult for a nanocrystal to escape its box. Thus, the poor stability properties of colloidal nanocrystals in general, which cause purification and storage problems, can be improved by sealing those nanocrystals inside the desired dendron boxes. Further, the performance of solid state devices made of semiconductor nanocrystals, such as LEDs and solid state lasers, can be significantly enhanced by the improved stability of box-nanocrystals using semiconductor nanocrystals. In addition, the thin cross-linked dendron monolayer of the box-nanocrystals should also be ideal for efficient charge injection for solid state optoelectronic devices.

Typically, the stability of box-nanocrystals and dendron-nanocrystals against thermal treatments depends on the composition of the inorganic nanoparticle core. For example, under the same conditions described herein for the CdSe nanocrystals (100° C. and vacuum), $Fe_3O_4$ dendron-nanocrystals survived a twenty-hour thermal treatment.

Photochemical Stability of Box-Nanocrystals

Figure 10:
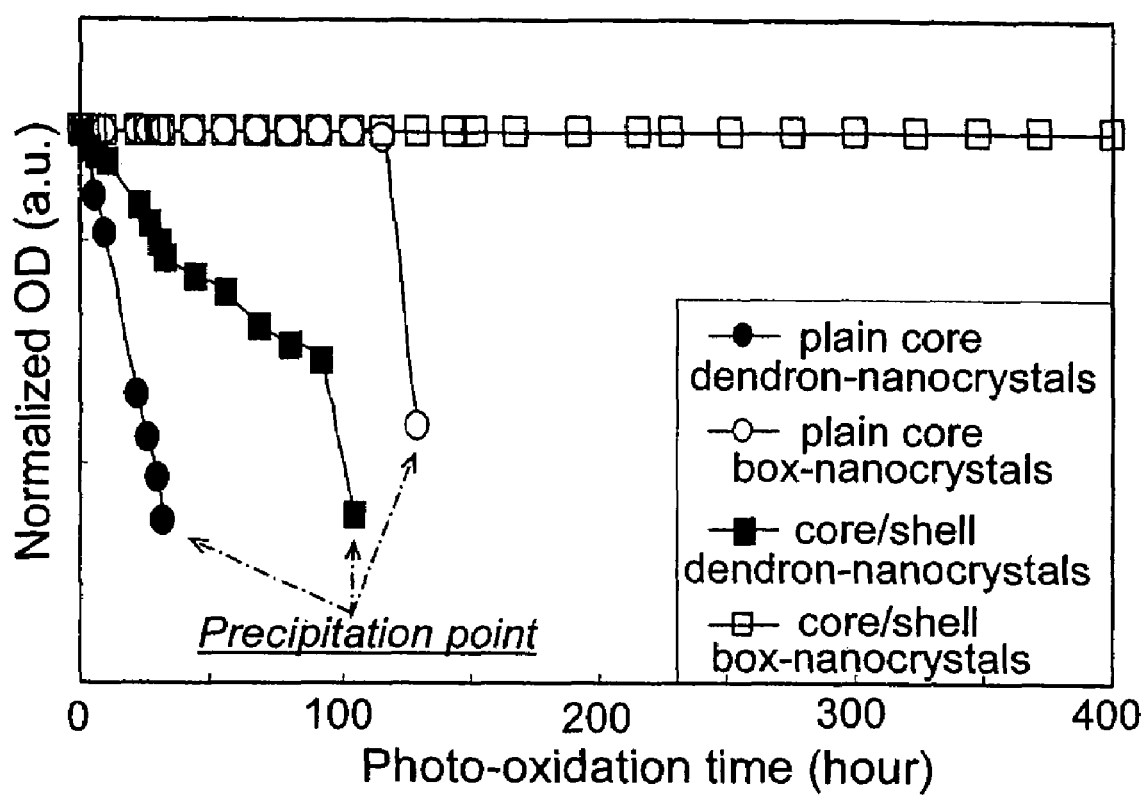
FIG. 10 provides the results of a photochemical stability study of the nanocrystals of this invention under UV radiation in air. The normalized OD (optical density, equivalent to absorbance) at the first absorption peak position is plotted against UV irradiation time. This figure illustrates the relative stability scale for the various nanocrystals of this invention is as follows. The CdSe/CdS core/shell box-nanocrystals are more stable than the plain CdSe core box-nanocrystals, which are more stable than the CdSe/CdS core/shell dendron-nanocrystals, which are more stable than the plain CdSe core dendron-nanocrystals. The box-nanocrystals were prepared through the RCM route.

The photochemical stability of box-nanocrystals in air under UV radiation was studied following the established procedure (14,15). FIG. 10 illustrates the results for four different samples, CdSe dendron-nanocrystals, CdSe box-nanocrystals, CdSe/CdS core/shell dendron-nanocrystals, and CdSe/CdS core/shell box-nanocrystals. The relative stability scale for the various nanocrystals of this invention is as follows. The core/shell box-nanocystals are more stable than the plain core box-nanocrystals, which are more stable than the core/shell dendron nanocrystals, which are more stable than the plain core dendron nanocrystals.

The dendron-nanocrystals of the current ligand system were moderately stable against photo-oxidation. The plain core CdSe dendron-nanocrystals were gradually photo-oxidized and precipitated out of the solution after about 35 hours. In contrast, the CdSe/CdS core/shell dendron-nanocrystals were significantly more stable than the plain core dendron-nanocrystals, and its precipitation occurred after about 100 hours inside a photo-oxidation chamber.

The box-nanocrystals of both the plain core and the core/shell nanocrystals were much more stable than the corresponding non-cross-linked dendron-nanocrystals. For the plain core box-nanocrystals, there was no observable oxidation of the inorganic core detected after the sample was in the photo-oxidation chamber for about 125 hours, although precipitation was observed to be quite rapid. In the case of the core/shell box-nanocrystals, photo-oxidation was not detected for 27 days (650 hours). After 27 days exposure in the photo-oxidation chamber, the precipitation of the nanocrystals occurred in a rapid fashion and was very similar to that of the CdSe box-nanocrystals shown in FIG. 10. The precipitation point of the core/shell box-nanocrystals does not appear in FIG. 10 because of its different time scale.

Photoluminescence of Semiconductor Core/Shell Nanocrystals Upon Oxidation

The core/shell nanocrystals of this invention are typically prepared in the presence of surface amine ligands. The photoluminescence (PL) of the core/shell nanocrystals partially remained after the replacement of these surface amine ligands by the thiol-based dendrons such as the ones shown in FIG. 1. Further, the cross-linking and the thermal sintering under vacuum did not change the emission properties of the core/shell dendron-nanocrystals nor the box-nanocrystals.

The PL properties of the core/shell nanocrystals varied in an interesting fashion under chemical oxidation and photo-oxidation conditions, as the PL brightness decreased slightly at the beginning stages of the chemical or photo-chemical oxidation. After this initial stage, the PL brightness typically increased significantly, usually with at least a two-fold increase in the relative intensity of the PL peak. In all experiments performed so far, this increase in PL brightness was always associated with a slight blue shift of the absorption spectrum. A similar PL brightening was also observed if the core/shell dendron-nanocrystals were stored in air with room light after several weeks.

Figure 11:
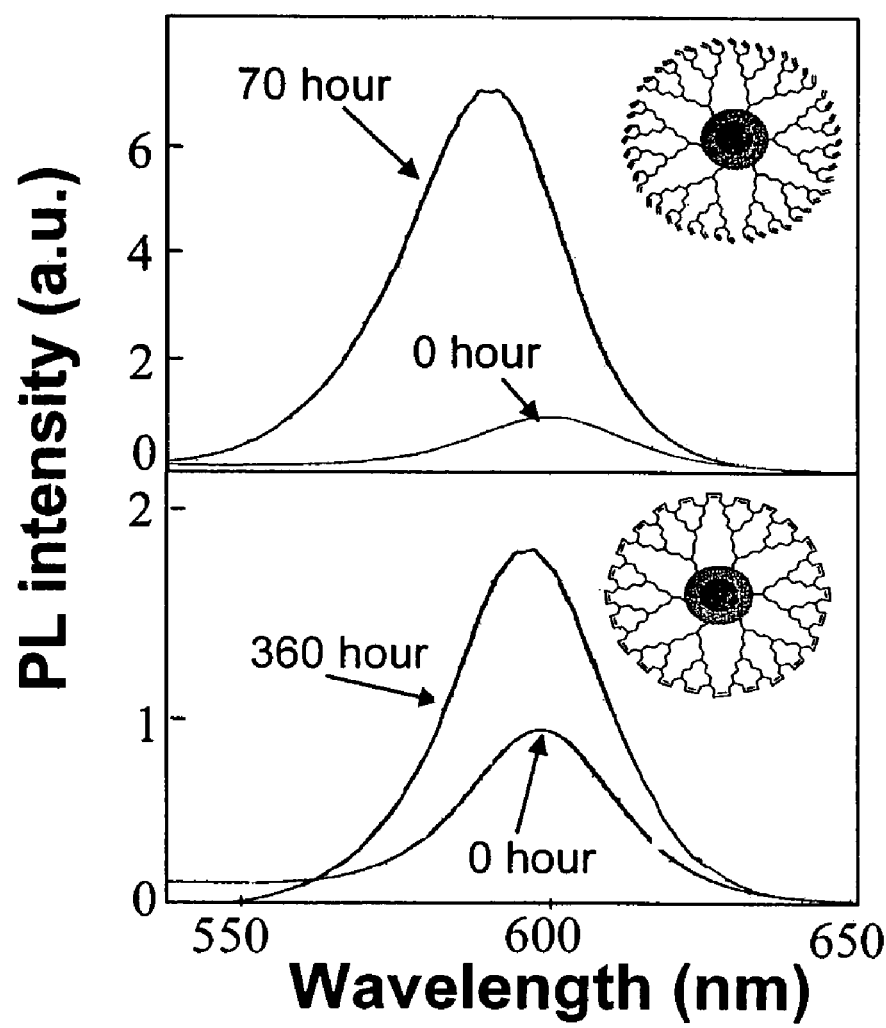
FIG. 11 demonstrates the photoluminescence (PL) spectra of the CdSe/CdS core/shell dendron-nanocrystals (top) and CdSe/CdS core/shell box-nanocrystals (bottom) of this invention, in particular, the intensity increase and blue shift of the of the PL spectra of the nanocrystals upon photo-oxidation.

FIG. 11 demonstrates the photoluminescence spectra of the CdSe/CdS core/shell dendron-nanocrystals (top) and CdSe/CdS core/shell box-nanocrystals (bottom) of this invention, in particular, the intensity increase and blue shift of the nanocrystals upon photo-oxidation. As FIG. 11 illustrates, generally, the PL brightening of core/shell nanocrystals through photo-oxidation was more easily controlled than PL brightening by chemical oxidation. Further, it was easier to achieve PL brightening for the core/shell dendron-nanocrystals than for the core/shell box-nanocrystals. If the oxidation process was stopped, the brightened nanocrystals maintained their PL efficiency at the stop point. In this way, the PL quantum yield of the brightened core/shell dendron-nanocrystals could be stabilized and maintained at about 20 to 30%.

The plain core nanocrystals, including both dendron-nanocrystals and box-nanocrystals, did not emit immediately upon replacing the original surface amine ligands with the thiol based dendron ligands. This was true even when those highly luminescent CdSe nanocrystals isolated at the "bright point" (of highest PL quantum yield) in a growth reaction (see. Qu, et al., Journal of the American Chemical Society, 2002, volume 124, page 2049-2055) were employed for the surface replacement. In addition, no subsequent treatments including cross-linking, thermal sintering, chemical oxidation, and photochemical oxidation, revived a noticeable PL for the plain core nanocrystals.

Formation of Empty Dendron-Boxes

Figure 12:
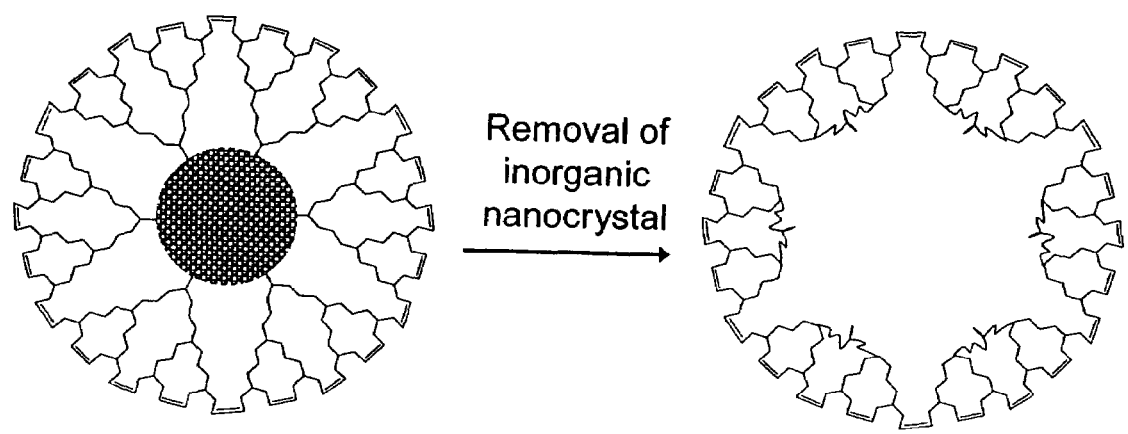
FIG. 12 illustrates a general reaction scheme for the formation of empty dendron-boxes by removing the inorganic core of each box-nanocrystal.

One aspect of this invention is the use of ring-closing metathesis (RCM) reactions for cross-linking the branches of the dendron ligands bound to the surface of the nanocrystals described herein. The resulting structures in which a nanoparticle is encapsulated in a dendren box is termed a box-nanocrystal. In some cases, the nanocrystal core of the box-nanocrystal was chemically removed to form an empty dendren box. These dendrien boxes are expected to be useful as molecular imprinting structures and drug delivery carriers. FIG. 12 illustrates a general reaction scheme for the formation of nanometer-sized empty dendron-boxes by removing the inorganic core of each box-nanocrystal. As illustrated in FIG. 5, the mass spectra of the solutions obtained by digestion of CdSe dendron-nanocrystals before and after the cross-linking reaction revealed the intact, cross-linked, nanometer-sized polymer capsule was obtained from digestion of the box-nanocrystal.

The size distribution of empty dendron boxes revealed by mass spectroscopy and illustrated in FIG. 5 was quite narrow. Typically, the FWHM (full-width at half maximum) of the mass peak was about 2-4 dendron units, which corresponds to about a 5-10% standard deviation in size. This distribution matched quite well with the size distribution of the nanocrystals sealed inside the boxes. From this information, it is believed that the surface coverage of the dendron ligands among a batch of nanocrystals was fairly uniform, although surface coverage might vary from batch to batch, depending on the particular reaction conditions employed in that batch. Further, cross-linking reactions did not affect this uniformity, although an approximately 10-30% loss of the dendrons was observed in the cross-linking process.

The inorganic nanocrystals disclosed herein were able to escape the dendron boxes after the chemical bonds between the inorganic nanocrystals and the ligands boxes were destroyed. Such permeability is desirable for drug delivery, molecular imprinting, and a variety of host-guest chemical applications. Such dendron boxes are likely to be the largest empty dendron boxes with a very narrow size distribution currently available. In contrast to the large cavity of the box, the wall of the box based on a G3 dendron itself is quite thin, which is also expected to make these dendron-boxes useful for molecular imprinting and other types of host-guest applications.

Conjugation Chemistry of the Box-Nanocrystals

Figure 15:
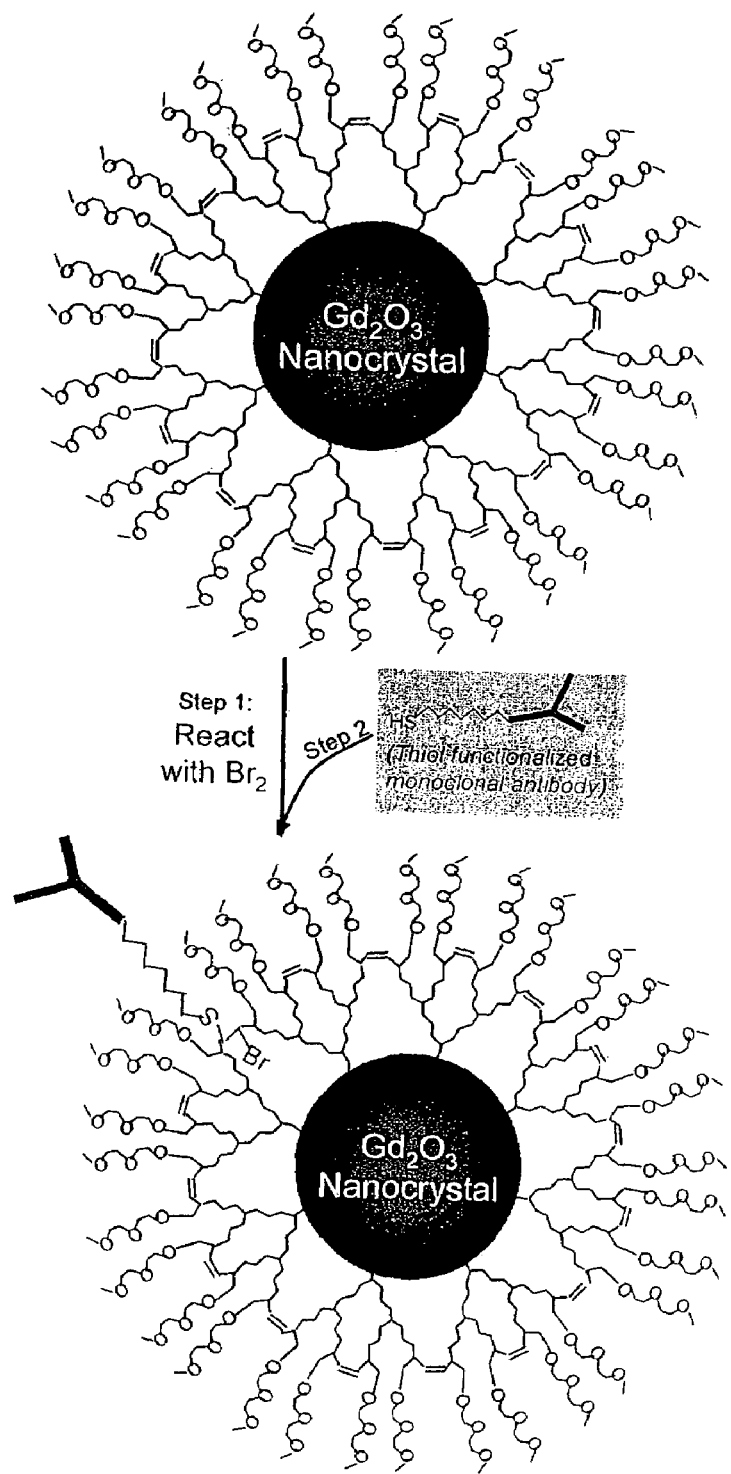
FIG. 15 illustrates one reaction scheme for immobilizing a thiol functionalized, conjugate monoclonal antibody onto a $Gd_2O_3$ box-nanocrystal. For most MRI applications, activation and conjugation on multiple double bonds are acceptable.

In a further aspect of this invention, the nanocrystals of this invention were chemically coupled to certain chemical or biochemical functional groups, which tailored them for various biochemical or medical applications. This process was relatively simple for box-nanocrystals due to their superior stability and robust chemical and physical behavior. A range of conjugation chemistry of box-nanocrystals is possible, varying according to differences in the structure and properties of the box-nanocrystal's periphery, backbone, bonding, and the inorganic core. For instance, the terminal carbon-carbon double bonds of the box-nanocrystals shown in FIG. 2 can readily react with $Br_2$ under mild conditions to afford bromo-functionalized periphery of the box-nanocrystal. Subsequently, the bromo functional groups can react with amines, hydroxyl groups, and many other functional groups to afford a product tailored to a specific application. FIG. 15 is presented as an example.

Figure 13:
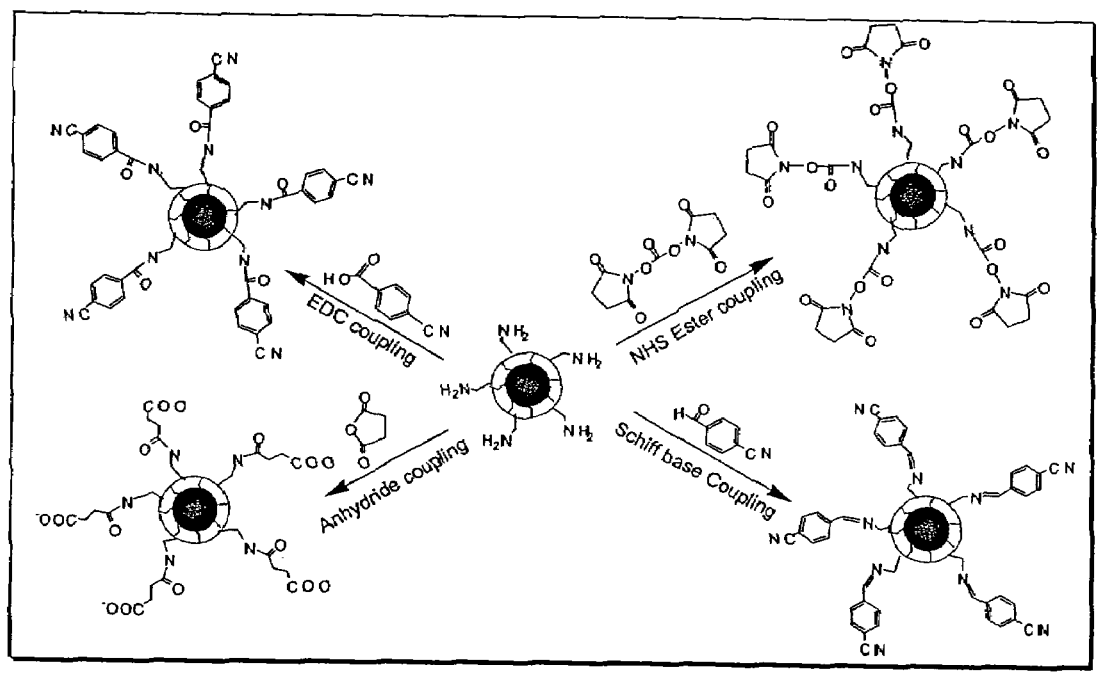
FIG. 13 provides a reaction scheme illustrating several representative coupling reactions tested for the amine box-nanocrystals. The results of these different coupling reactions are demonstrated by the FTIR specta in FIG. 14.
Figure 14:
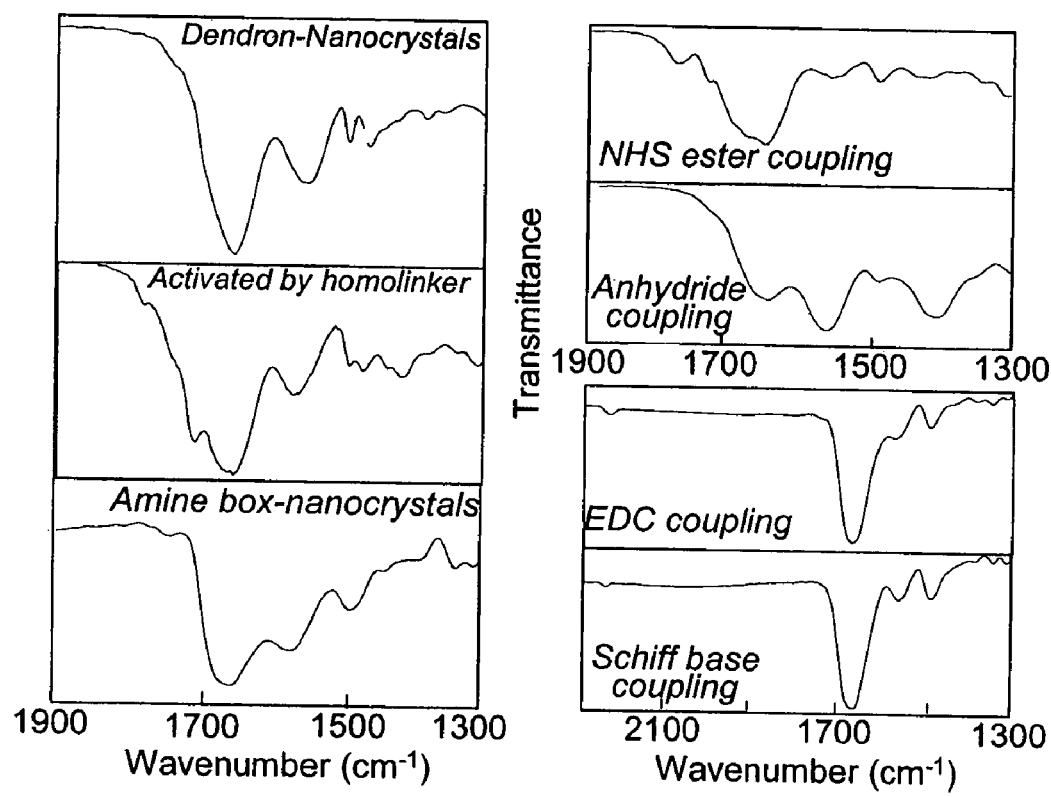
FIG. 14 provides a series of FTIR spectra of nanocrystal-ligand complexes. Left. FTIR spectra demonstrating the formation of amine box-nanocrystals. Right. FTIR spectra of the coupling products of the amine box-nanocrystals formed by the different coupling reactions shown in FIG. 13.

The amine box-nanocrystals shown in FIG. 3 provide examples of several of the many possible conjugation strategies of box-nanocrystals of this invention. The coupling chemistry of amine box-nanocrystals was found to be diverse and to occur in high yield reactions. FIG. 13 illustrates four different coupling strategies commonly used in bio-conjugation, and tested for the amine box-nanocrystals. Fourier transform infrared spectroscopy (FTIR) was used to monitor the progress of the conjugate chemistry reactions of the dendron-nanocrystals. Reagents with distinguishable IR fingerprints were employed for these coupling reactions. FIG. 14 illustrates the FTIR spectra of the dendron-nanocrystals, amine box-nanocrystals and the coupling products of the box-nanocrystals resulted from different coupling reactions. The assignments of the IR fingerprint peaks are provided in Table 1. These assignments were assisted by coupling reactions with small molecule analogs that were also carried out and the IR spectra of the purified products which were recorded for reference.

TABLE 1

The IR fingerprint spectra of the dendron-nanocrystals, amine box-nanocrystals of FIG. 3, and the coupling products of the amine box-nanocrystals as shown in FIG. 13. A portion of these spectra are illustrated in FIG. 14.

| Species | Fingerprint Peaks (cm$^{-1}$) | Assignments |
|---|---|---|
| G3-OH dendron-nanocrystals | 1661 | C=O stretch (amide I) |
|  | 1566 | N—H bend (amide II) |
| Activated G3-OH | 1774 | C=O stretch (ester) |
| Dendron-nanocrystals by homolinker | 1669 | C=O stretch (NHS amide I) |
|  | 1655 | C=O stretch (amide I) |
|  | 1556 | N—H bend (amide II) |
| Amine box-nanocrystals | 1670 | C=O stretch (amide I) |
|  | 1567 | $NH_2$ deformation and N—H bend |
| NHS ester coupling product | 1770 | C=O stretch (ester) |
|  | 1731 | C=O stretch (NHS amide I) |
|  | 1664 | C=O stretch (amide I) |
|  | 1556 | N—H bend (amide II) |
| Anhydride coupling product | 1651 | C=O stretch (amide I) |
|  | 1550 | carboxylate ion asymmetrical stretch |
|  | 1400 | carboxylate ion symmetrical stretch |
| EDC coupling product | 2226 | C≡N stretch |
|  | 1661 | C=O stretch (amide I) |
|  | 1549 | N—H bend (amide II) |
| Schiff base coupling product | 2226 | C≡N stretch |
|  | 1655 | C=N and C=O stretch (amide I) |
|  | 1553 | N—H bend (amide II) |

Conjugation of Bio-Functional Species onto Box-Nanocrystals

The conjugation strategies described herein can readily be used for conjugation of bio-functional species onto box-nanocrystals. For the box-nanocrystals assembled by RCM reactions, bio-conjugation can be readily performed by activating the double bonds that result from the RCM reaction, with bromo groups, one example of which is illustrated in FIG. 15. Thus, FIG. 15 illustrates one reaction scheme for immobilizing a thiol functionalized, conjugate monoclonal antibody onto a $Gd_2O_3$ box-nanocrystal. For most MRI applications, activation and conjugation on multiple double bonds are acceptable.

Using the amine box-nanocrystals shown in FIG. 3 as a model system, the bio-accessibility of the box-nanocrystals was demonstrated by coupling biotin onto the surface of the nanocrystals using one of the above demonstrated coupling strategies, namely NHS ester coupling (see. Guo, et al., Chemistry of Materials, 2003, volume 15, page 3125-3133). The resulting nanocrystals are named as biotinylated box-nanocrystals. The commercially available Sulfo-NHS-biotin worked well to react with the amine box-nanocrystals. The reaction was carried out for a relatively long period of time in order to reduce the free biotin reagent in the system. By doing so, the further separation of the resulting biotinylated box-nanocrystals from free biotin was unnecessary.

With the incorporation of more biotin units on each nanocrystal surface, the original hydrophilic box-nanocrystal gradually became hydrophobic due to the poor hydrophilic nature of the biotin reagent. Accordingly, the biotinylated box-nanocrystals with high biotin density on the surface precipitated out from the typical reaction solution (DMSO:$H_2O$ is 1:1 by volume). Therefore, the amount of biotin on each nanocrystal may be controlled in such a manner that the nanocrystal maintains its solubility and at the same time exhibits maximum number of binding sites for avidin.

The biotinylated core/shell box-nanocrystals exhibited the same stability as amine box-nanocrystals. For example, the PL intensity of biotinylated core/shell box-nanocrystals remained constant for hours under the standard photo-oxidation conditions, and for at least several months under ambient conditions. The excellent stability of bio-conjugated box-nanocrystals provides an essential basis for developing quantitative binding assays using bio-functional box-nanocrystals.

Detection of Bio-Active Species Using Box-Nanocrystals

Generally, bio-detection systems using semiconductor nanocrystals have been at a qualitative or non-reproducible level largely because of the instability of the nanocrystals employed. In contrast, this invention provides quantitative and reproducible detection of bio-targets using the box-nanocrystals disclosed herein.

Figure 16:
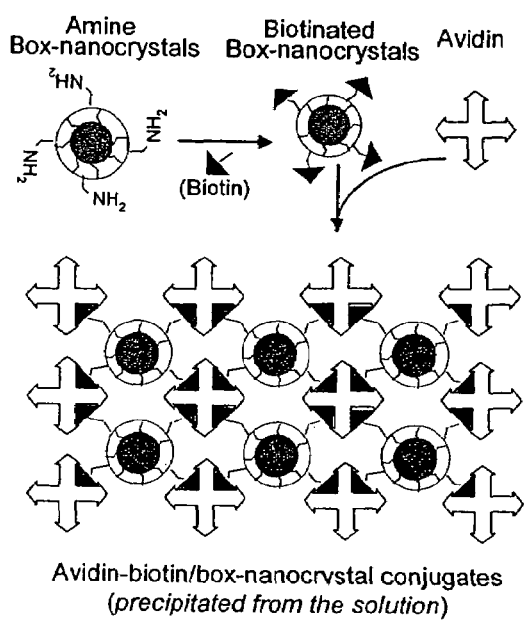
FIG. 16 illustrates the following. Left: A reaction procedure for the formation of Avidin-biotin/box-nanocrystal conjugates is provided, from reacting Avidin with a biotinated box-nanocrystal. Right: The quantitative results of this reaction procedure are illustrated from the UV-Vis and PL measurements upon the formation of the conjugates. These spectra also show the results using two controls, namely: (1)
Figure 16:
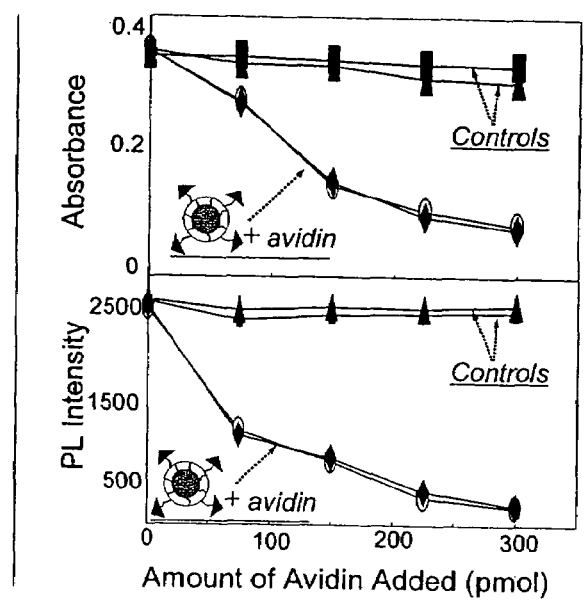

Thus, another aspect of this invention is the bio-medical applications of box-nanocrystals, which were demonstrated using biotin-avidin binding assay with biotinylated box-nanocrystals. Avidin is a glycoprotein which contains four identical subunits, with each subunit possessing one binding site for one biotin molecule. The strong, yet non-covalent, binding between avidin and biotin makes it very useful in bio-conjugation chemistry. The biospecificity of the avidin-biotin interaction is similar to antibody-antigen or receptor-ligand recognition, but is characterzed by a greater affinity constant Upon the addition of a certain amount of avidin (75 pmol) in PBS buffer to the biotinylated box-nanocrystals in DMSO and $H_2O$ solution (1:1/v:v), the clear solution turned to turbid immediately, indicating the formation of avidin-biotin/box-nanocrystal conjugates. This turbid solution was centrifuged for a few minutes to obtain a clear top solution for UV-Vis and PL measurements. The addition of avidin was continued until the solution was almost colorless. FIG. 16 (left) schematically illustrates a reaction procedure for the formation of avidin-biotin/box-nanocrystal conjugates, by reacting avidin with a biotinated box-nanocrystal. FIG. 16 also illustrates the quantitative results of this reaction procedure from the UV-Vis and PL measurements upon the formation of the conjugates. These spectra also show the results using two controls, namely: (1) biotinated box-nanocrystals plus plain PBS buffer; and (2) amine box-nanocrystals plus avidin in PBS buffer. A picomole amount of avidin could be readily detected, and the results from both UV-Vis and PL measurements of two parallel detection reactions were almost identical.

Non-specific binding of the box-nanocrystals to biological targets was also examined. Three sets of experiments were performed to exclude non-specific binding in this system. In the first control experiment, the same volume of PBS buffer without avidin was added into the biotinylated box-nanocrystal solution, and no precipitate was observed. The UV-Vis absorbance and PL intensity after calibration of dilution effect kept as constants with repeated centrifugation and addition of the buffer solution (FIG. 16, right). This result revealed that the biotinylated box-nanocrystals are stable in the buffer solution.

The second control experiment was designed to study the non-specific binding of avidin with the amine groups on the surface of the box-nanocrystals. The same amount of avidin was added to the solution of amine box-nanocrystals under exactly the same conditions for the biotinylated box-nanocrystal system. Again, no precipitation was observed using the amine box-nanocrystals, and no change of either UV-Vis absorbance and/or PL intensity was observed during the continuous addition of the avidin solution (FIG. 16, right). These results indicated that the box-nanocrystals showed no substantial non-specific binding in this system.

The third experiment was designed to directly verify that the precipitation of the nanocrystals observed in FIG. 16 was indeed due to the specific binding between avidin and biotin. The interaction between avidin and biotin, much like other specific bindings in biological systems, is not covalent although it is a strong interaction. If avidin is denatured by heating, the specific binding will disappear, and biotinylated box-nanocrystals will be released into solution. Experimentally, after the avidin-biotin/box-nanocrystal conjugates in the bottom of the mother solution were heated at 70° C. for about 2 h, the color of the solution came back. The UV-Vis absorbance and PL intensity were almost recovered to the original values of the biotinylated box-nanocrystal solution before the addition of avidin. This result strongly suggests that the precipitation illustrated in FIG. 16 was due to the specific binding between the avidin molecules added and the biotin molecules chemically attached on the surface of the box-nanocrystals.

The present invention is further illustrated by the following examples, which are presented for illustration purposes and which are not to be construed in any way as limiting the scope of the present invention. On the contrary, it is to be clearly understood that resort may be had to various other embodiments, modifications, and equivalents thereof which, after reading the description herein, may suggest themselves to one of ordinary skill in the art without departing from the spirit of the present invention or the scope of the appended claims.

General experimental information and sources of precursor chemicals are as follows. Triphenylmethanol, 2-aminoethanethiol hydrochloride, bromoactyl bromide, diallyamine, triethylsilane, trifluoroacetic acid (TFA), tetramethylammonium hydroxide, N,N'-disuccinimidyl carbonate (DSC), 4-cyanobenzaldehyde, 4-cyanobenzoic acid, succinic anhydride, 4-(dimethylamino)pyridine (DMAP), ethylenediamine, anhydrous methyl sulfoxide (DMSO), trioctylphosphine oxide (TOPO, technical grade, 90%), trioctylphosphine (TOP, technical grade, 90%) cadmium acetate hydrate (99.99+%), selenium powder (100 mesh, 95%), anhydrous toluene (99.8%), Celite™, Grubbs' catalyst (second generation) were all purchased from Aldrich (Milwaukee, Wis.). Anhydrous ethyl ether, benzene, chloroform, N,N-dimethylformamide (DMF), acetone, ethyl acetate, methanol, triethylamine and $K_2CO_3$, were all purchased from EM Science (Cincinnati, Ohio). Unless otherwise specified, all chemicals and reagents were used as received without further purification. Immunopure avidin, Sulfo-NHS-biotin were purchased from Pirece.

EXAMPLE 1

General Synthesis of a Symmetric Generation 3 (G3) Dendron Ligand

A symmetric G3 dendron ligand 6 was synthesized as shown in FIG. 17. The reagents, conditions, and yields for the reactions shown in FIG. 17 are as follows: a=2-aminoethanethiol hydrochloride, TFA, 25° C., 30 min, 85%; b=1 M NaOH, 96%; c=N-(tert-butoxycarbonyl)aziridine, $CH_3CN$, reflux 3 days, 67%; d=TFA, 30 min, 92%; e=1 M NaOH, 98%; f=THF, $K_2CO_3$, reflux, 12 hours, 62%; g=TFA, triethylsilane, 95%; h=ethyl acetate, 72%. The focal point of the dendron ligands, a thiol group, was the binding site to surface cadmium atoms of the nanocrystals. In the synthesis, a triphenylmethyl group was applied to protect the thiol group as shown. With this protection, dendron precursors were stable under both acidic and basic conditions. Compound 2, 2-tritysulfanyl-ethylamine was obtained upon the treatment of triphenylmethanol with 2-aminoethanethiol hydrochloride in trifluroacetic acid (TFA), followed by neutralization with aqueous NaOH. The acetonitrile solution of 2 was refluxed with N-(tert-Butoxycarbonyl)aziridine to give the tert-butoxycarbonyl (BOC)-protected first generation of dendron. Compound 3 was obtained as a yellow oil after the deprotection of the BOC group with TFA. The reaction of bromoacetyl bromide with diallyl amine at 0° C. afforded compound 4, N,N-diallyl-2-bromo-acetamide. The triphenylmethyl-protected G3 dendron ligand was readily prepared by N-alkylation of compound 3 with active α-bromide 4 in the presence of aqueous $K_2CO_3$. Dendron ligand 6 was finally obtained by treatment of 5 with TFA and triethylsilane as shown. Specific synthetic details are provided in the following examples.

EXAMPLE 2

Synthesis of 2-Tritylsulfanyl-ethylamine (2)

Triphenylmethanol (22.9 g, 88 mmol) was added to a solution of 2-aminoethanethiol hydrochloride in trifluroacetic acid (TFA, 40 mL). The resulting solution was stirred at room temperature for about 40 min. The TFA was then removed under reduced pressure and the residue was triturated with diethyl ether. The white precipitate that formed was filtered, partitioned with aqueous NaOH (40 mL, 1N), and extracted with ethyl acetate (3×50 mL). The combined organic layers were dried over $Na_2SO_4$. The product was obtained as a white solid after solvent evaporation (23.8 g, yield 85%). ESI-MS(m/z): 320 (M+H$^+$). $^1$H NMR $\delta_D$ (CDCl$_3$): 7.21~7.43 (m, 15H, phenyl), 2.58 (t, 2H, SCH$_2$), 2.32 (t, 2H, CH$_2$N).

EXAMPLE 3

Synthesis of Bis-(2-amino-ethyl)-(2-tritylsulfanyl)-amine (3)

A CH$_3$CN (135 mL) solution of compound 2 (9.3 g, 29 mmol) and N-(tert-butoxycarbonyl)aziridine (12.3 g, 87 mmol) was refluxed for 3 days. The solvent was then removed under reduced pressure and the residual oil was purified by silica gel column chromatography with CHCl$_3$ as the eluent. This procedure provided 12.3 g of BOC-protected G1 dendron as light yellow solid. This solid was then treated with TFA, dried under reduced pressure, and partitioned with aqueous NaOH to give compound 3 as yellow oil (7.9 g, yield 68%). ESI-MS (m/z): 406 (M+H$^+$). $^1$H NMR $\delta_D$ (CDCl$_3$): 7.23~7.44 (m, 15H, phenyl), 2.78 (t, 2H, SCH$_2$), 2.60~2.70 (m, 4H, CH$_2$NH$_2$), 2.27~2.35 (m, 6H, CH$_2$N).

EXAMPLE 4

Synthesis of N,N-diallyl-2-bromo-acetamide (4)

Bromoacetyl bromide (45 g, 0.22 mol) in ethylacetate (25 mL) was added dropwise to a solution of diallyl amine (9.6 g, 0.1 mol), Et$_3$N (15 mL), in ethyl acetate (50 mL) at 0° C. The reaction was then warmed to ambient temperature, and the stirring was continued for about 3 h. The resulting mixture was washed with saturated NaHCO$_3$ solution (3×100 mL) and dried over Na$_2$SO$_4$. The evaporation of the solvent gave 16.2 g of product as a light yellow oil (yield 75%). ESI-MS (m/z): 218 (M+H$^+$). $^1$H NMR $\delta_D$ (CDCl$_3$): 5.75 (m, 2H, CH), 5.19 (m, 4H, CH$_2$), 3.95 (d, 4H, NCH$_2$), 3.81 (2, 2H, BrCH$_2$).

EXAMPLE 5

Synthesis of N,N-dially-2-({2-[[2-bis-diallylcarbamoylmethyl-amino)-ethyl]-(2-trutylsulfanyl-ethyl)-amino]-ethyl}-daillylcarbamoylmethyl-amino)-acetamide (5)

Compound 4 (0.9 g, 4.1 mmol) was added to a solution of compound 3 (0.4 g, 1 mmol), K$_2$CO$_3$ (0.84 g, 6 mmol, in 3 mL of H$_2$O) in THF (15 mL). The reaction mixture was then heated at 65° C. overnight, after which time the solvent was removed under reduced pressure. The residue was purified by silica gel column chromatography, eluted with CHCl$_3$/MeOH (85:15/v:v) to obtain a light yellow product (0.7 g, yield 73%). ESI-MS (m/z): 954 (M+H$^+$). $^1$H NMR $\delta_D$ (CDCl$_3$): 7.21~7.33 (m, 15H, phenyl), 5.68 (m, 8H, CH), 5.07 (m, 16H, CHCH$_2$), 3.44~3.88 (m, 24H, COCH$_2$, CH$_2$CHCH$_2$), 2.81 (m, 2H, SCH$_2$), 2.31 (m, 10H, NCH$_2$).

EXAMPLE 6

Synthesis of N,N-dially-2-({2-[[2-bis-diallylcarbamoylmethyl-amino)-ethyl]-(2-mercapto-ethyl)-amino}-ethyl}-diallylcarbamoylmethyl-amino)-acetamide (6)

Triethylsilane (0.1 mL) was added to a solution of 5 (0.5 g, 0.5 mmol) in trifluroacetic acid (TFA, 10 mL). The white precipitate that formed upon triethylsilane addition was removed by filtration through Celite™. The TFA was then removed under reduced pressure to give the product as a light yellow oil (0.34 g, 95%). ESI-MS (m/z): 712 (M+H$^+$). $^1$H NMR $\delta_D$ (CDCl$_3$): 5.68 (m, 8H, CH), 5.07 (m, 16H, CHCH$_2$), 3.44~3.88 (m, 24H, COCH$_2$, CH$_2$CHCH$_2$), 2.75 (m, 2H, SCH$_2$), 2.31 (m, 10H, NCH$_2$).

EXAMPLE 7

Synthesis of CdSe and CdSe/CdS Core/Shell Nanocrystals

Trioctylphosphine oxide (TOPO)-capped or amine-capped CdSe nanocrystals were synthesized using the standard "greener" methods reported previously. (See: Aldana, J.; Wang, Y.; Peng, X. *J. Am. Chem. Soc.* 2001, 123, 8844; Qu, L.; Peng, Z. A.; Peng, X. *Nano Lett.* 2001, 1, 333; and Qu, L.; Peng, X. *J. Am. Chem. Soc.* 2002, 124, 2049-2055; which are incorporated by reference in their entireties.) The typical size of the nanocrystals used in this work was about 3.3 nm with the first excitonic absorption peak at 550 nm. The CdSe/CdS core/shell nanocrystals were synthesized through the solution atomic layer epitaxy (SALE) method. The core size of the core/shell nanocrystals was about 3.5 nm and the shell thickness was about 1.5 monolayers of CdS.

EXAMPLE 8

Synthesis of an Asymmetric Generation 3 (G3) Dendron Ligand (FIG. 18)

FIG. 18 provides a synthetic scheme for the preparation of an asymmetric Generation 3 (G3) dendron ligand in two parts. Part I provides a synthesis of the tertiary amine 4, which is used in the final step of Part II to form the asymmetric G3 dendron.

Synthesis of tosylated triethylene glycol monomethyl ether 2. To a solution of triethylene glycol monomethyl ether 1 (32.8 g, 0.2 mol), triethyl amine (20.4 g, 0.2 mol) and pyridine (2.0 g, 0.026 mol) in CH$_2$Cl$_2$ (100 mL), and p-toluene sulfonyl chloride (42 g, 0.22 mol) in CH$_2$Cl$_2$ (100 mL) was added slowly over a period of 2 h in an ice-bath. The reaction mixture was then stirred for 36 h at room temperature, after which the mixture was filtered and the solvent was evaporated in vacuo to give a brown oil. This oily residue was purified by column chromatography on silica gel with Hexane:CHCl$_3$(5:1) then EtOAc to give the product as a colorless oil (54.6 g, 86%).

Synthesis of the secondary amine 3. To a solution of allylamine (21.2 g, 372 mmol) in THF (100 mL) was added tosylated triethylene glycol monomethyl ether (2) in THF (50 mL). The reaction mixture was stirred at 50° C. for 24 h then additional allylamine (10.5 g, 186 mmol) was added and stirred for 12 h. The reaction mixture was partitioned between CHCl$_3$ (100 mL) and 2N HCl (100 mL). The aqueous layer was separated and washed with CHCl$_3$ (100 mL×2). To an acidic aqueous layer was added 2N NaOH until the pH reached about 11. The aqueous layer was extracted with $CHCl_3$ (100 mL×6) and the organic layers were combined and dried over $Na_2SO_4$. The solvent was evaporated from this solution to give the product as a yellowish oil (14.0 g, 93%).

Synthesis of the tertiary amine 4. To a solution of secondary amine 3 (5.0 g, 24.6 mmol) and triethylamine (2.49 g, 24.6 mmol) in EtOAc (100 mL) was added bromoacetyl bromide (9.93 g, 49.2 mmol) in EtOAc (20 mL) slowly in the period time of 1 h in an ice bath. The reaction mixture was stirred for additional 3 h in an ice bath. To this mixture was added saturated $NaHCO_3$ (20 mL) slowly. The organic layer was separated and washed with $NaHCO_3$ (20 mL) and water (20 mL×2), and then dried over $Na_2SO_4$. The solvent was evaporated from this solution to give a pale brown oil. The oil was purified by column chromatography on silica gel with $CH_2Cl_2$:EtOAc (3:2/v:v) to give the product as a pale yellow oil (4.0 g, 50%).

Synthesis of the N-protected diamine 6. To a solution of 3,5-dihydroxybenzoic acid methyl ester 5 (10.8 g, 60.0 mmol) and $K_2CO_3$ (37.2 g, 270 mmol) in DMF (100 mL) was added N-Boc protected 2-bromoethylamine (35.2 g, 147 mmol) in DMF (20 mL). The reaction mixture was stirred overnight at 50° C. The reaction mixture was then filtered and the solvent was evaporated to give brown oily residue. The residue was dissolved in $CHCl_3$ (150 mL) then washed with water (100 mL×2) and dried over $MgSO_4$. The solvent was evaporated to give a pale yellow oil. The oily residue was recrystallized from EtOAc:hexane to give the product as a white solid (20.1 g, 74%).

Synthesis of diamine hydrochloride 7. Boc-protected diamine 6 (21 g, 46.2 mmol) was dissolved in $CH_2Cl_2$ (100 mL) and diethyl ether (100 mL). To this solution was added concentrated HCl (50 ml) and this mixture was then stirred overnight. The solvent was then evaporated to give the product as a white precipitate. This solid (14.2 g, 94%) was then dried under vacuum.

Synthesis of asymmetric G3 dendron 8. To a solution of hydrochloride salt 7 (0.67 g, 2.0 mmol) and triethylamine (2.0 g, 20.0 mmol) in THF (50 mL) and water (50 mL) was added the tertiary amine 4 in THF (10 mL). The reaction mixture was stirred for 2 days at 70° C. To this mixture was added EtOAc (100 mL) then the organic layer was separated. The aqueous layer was washed with EtOAc (100 mL×2) then the organic layers were combined. The combined organic layer was washed with 100 mL of $NaHCO_3$ (aq) and water (100 mL) then dried over $Na_2SO_4$. Evaporate the solvent to give brown oily residue. This oily residue was purified by column chromatography on silica gel with EtOAc:MeOH (2:1) to the product as a pale yellow oil (1.1 g, 45%).

The ester functionality in compound 8 can be transformed to carboxylic acid, hydroxamic acid, phosphonic acid, or other bonding groups following standard literature methods. For example, the ester functional group in compound 8 was transformed to carboxylic acid by basic hydrolysis and the carboxylic acid was further transformed to hydroxamic acid by its reaction with hydroxyl amine hydrochloride salt.

EXAMPLE 9

Surface Modification of Semiconductor and Noble Metal Nanocrystals with Dendron Ligands CdSe and CdSe/CdS core/shell nanocrystals were modified with dendron ligand 6 shown in FIG. 17 through a procedure modified from one previously reported (14,15). Typically, a 20-mg sample of trioctylphosphine oxide (TOPO)-capped CdSe nanocrystals in $CHCl_3$ was added to a solution of 150 mg of ligand in 15 mL of 1:1 ratio $MeOH/CHCl_3$ solvent, and the pH value of such solution was adjusted to 10.3 by the addition of tetramethylammonium hydroxide. The reaction was carried out in the dark, either at room temperature or elevated temperatures, overnight. In the case of primary amine-coated CdSe/CdS core/shell nanocrystals, the basic solution of ligand and nanocrystals was first set to reflux under nitrogen for 4 h, and then the solution was cooled to room temperature and stirred for 12 h. The resulting dendron-nanocrystals were precipitated with a minimum amount of diethyl ether, and separated by centrifugation and decantation. This procedure may be slightly altered for the preparation of noble metal and other semiconductor dendron-nanocrystals.

EXAMPLE 10

Surface Modification of Metal Oxide Nanocrystals with Dendron Ligands $Fe_3O_4$ nanocrystals were modified with dendron ligands using hydroxamic acid as the bonding group by the surface replacement of the original fatty acid ligands. $Fe_3O_4$ nanocrystals coated with fatty acids were synthesized by the suspension of the bare $Fe_3O_4$ nanocrystals formed by the co-precipitation of the ferrous chloride and ferric chloride under basic conditions. Typically, $Fe_3O_4$ nanocrystals coated with fatty acids were mixed with an equal molar amount of the dendron ligands in $CHCl_3$, and the reaction mixture was refluxed for a few hours. After the reaction was allowed to cool to room temperature, hexane was added to precipitate the resulting nanocrystals, which left the reaction byproducts in the supernatant. The resulting nanocrystals were soluble in a variety of solvents depending upon the terminal groups of the dendron ligands. A similar procedure was also applied for bare nanocrystals suspended in acidic aqueous solution (about pH=2), in which case, carboxylic acid was also be used as the bonding group.

EXAMPLE 11

Formation of Box-Nanocrystals through RCM Strategy

The terminal allyl groups of the dendron-nanocrystals were cross-linked to form box-nanocrystals using Grubbs' ruthenium alkylidene catalyst as shown in FIG. 19. Typically, the second generation of Grubbs' catalyst (2 mol % per alkene group) was added to a 1:1 ratio $CH_2Cl_2$/benzene solution ($10^{-5}$ M, based on alkene group) of the dendron-nanocrystals. The amount of ligands on the surface of nanocrystals was estimated by assuming a close packing of ligands on the surface of nanocrystals. The reaction was carried out in the dark at room temperature for 48 h. Portions of DMSO (20 μl) and silica gel (0.5 g) were then added to the reaction solution to remove the catalyst by a standard protocol. The box-nanocrystals were then precipitated out with a minimum amount of diethyl ether, and separated by centrifugation and decantation. The exact amount of chemicals and the procedures may vary if the composition and size of the nanocrystals differ.

EXAMPLE 12

Formation of Box-Nanocrystals through Dendrimer-Bridging Strategy

The dendrimer-bridging strategy for the formation of box-nanocrystals is illustrated in FIG. 3, which demonstrates how the cross-linking strategy provides global cross-linking of all dendron ligands on each nanocrystal and also functionalizes the nanocrystal with amine groups.

The homobifunctional cross-linker, N,N-disuccinimidyl carbonate (DSC, 8 mg) and 4-(dimethylamino)pyridine (DMAP, 6 mg) were added to a 15 mL solution of G3-(thiol)-OH-coated CdSe nanocrystals in dry DMSO. The absorbance at the first exciton peak of the 3.5 nm CdSe nanocrystals solution was 1.26. After the solution was stirred overnight, 2 mL of such solution was added dropwise into 15 mL of DMF solution containing 8 mg G2 dendrimer amine shown in FIG. 3. The resulting precipitates were isolated by centrifugation, and washed with water three times. The final amine-terminated box-nanocrystals were dissolved in HCl solution (pH=2) and immediately neutralized with aqueous NaOH to a pH of around 7. The amine box-nanocrystal solutions were dispersible between pH=2 to pH=9.

A similar cross-linking procedure was applied using ethylene diamine or tris(2-aminoethyl)amine, instead of G2 dendrimer amines. The products obtained from these cross-linking methods were different from the products obtained by dendrimer-bridging with diamine or trisamine as the linkage reagents were soluble in the coupling solutions. The resulting cross-linking products were used as references for the stability studies. The resulting nanocrystals showed some improvement of the stability in comparison to the original dendron-nanocrystals.

Depending on applications, the dendrimer used in this approach may be terminated with thiols, hydroxyl groups, ester groups, and the like. The reaction conditions listed above may vary from one type of inorganic nanocrystals to another.

EXAMPLE 13

Coupling Chemistry of the Amine Box-Nanocrystals

The amine box-nanocrystals were found to be very versatile for surface coupling reactions. Thus, FIG. 13 provides a reaction scheme illustrating several representative coupling reactions tested for the CdSe core and CdSe/CdS core/shell amine box-nanocrystals. A coupling reagent such as 4-cyanobenzaldehyde (2.5 mg) in 5 mL DMSO or dioxane was added to the solution of the amine box-nanocrystals formed as shown in FIG. 3, with the absorbance of the first absorption peak of the CdSe nanocrystals at 2.5. The pH value of this solution was adjusted to 8. After stirring overnight, the nanocrystals were precipitated out with a minimum amount of diethyl ether and acetone, and separated by centrifugation and decantation. The resulting nanocrystals were then redissolved and precipitated using a suitable solvents system which is determined by the terminal groups of the resulting nanocrystals, and separated by centrifugation and decantation at least three times to remove excess reagents. The final nanocrystal products were characterized by IR measurements by casting the nanocrystals solution onto the $CaF_2$ IR window. The results of these different coupling reactions are demonstrated by the FTIR specta in FIG. 14. Other methods were also applied to characterize the final products, for example, UV-Vis spectroscopy was useful for the Schiff base formation.

EXAMPLE 14

Coupling Reaction of Biotin onto the Amine Box-Nanocrystals to form Biotinylated Box-Nanocrystals Sulfo-NHS-biotin (2 mg) was added to 4 mL of either the core/shell CdSe/CdS or the CdSe amine box-nanocrystal solution in $H_2O$ and DMSO solvent (1:1/v:v). The absorbance of the first absorption peak of the nanocrystals in the solution was 2.5. After stirring this mixture overnight at room temperature, the slight turbid solution was centrifuged. The top clear solution was decanted to another vial for the bioassay. The amount of precipitate was found to be dependent on the ratio of biotin to the box-nanocrystals. It was observed that a high density of biotin on the surface of box-nanocrystals made them insoluble in either pure water or a solvent mixture containing water.

EXAMPLE 15

Avidin Detection Using Biotinylated Box-Nanocrystals

Detection of avidin using biotinylated box-nanocrystals was carried out by the addition of 10 μl of avidin solution (1 mg/mL in PBS buffer) to an optical cuvette containing 0.5 mL of the biotinylated box-nanocrystals with absorbance around 0.4 at the first absorption peak. A cloudy mixture formed upon the addition and was centrifuged for 5 minutes, the PL intensity and UV-Vis absorbance of the upper clear solution were monitored. The addition of avidin, centrifugation, and monitoring procedure was repeated until no more precipitate was formed. The precipitate of avidin-biotin/box-nanocrystal complexes was denaturized by heating to about 70° C.

EXAMPLE 16

Synthesis of a Dendron Ligand with Bi-Dentate Bonding Site (FIG. 20)

The synthetic steps of Example 16 are presented in FIG. 20.

Step 1. Synthesis of N-tert-butoxycarbonylaminoethylamine (2). Di-tert-butyldicarbonate (10.7 g, 50 mmol) dissolved in $CHCl_3$ (60 ml) was added dropwise to a solution of ethylenediamine (30.5 g, 0.5 mol) in 250 ml of $CHCl_3$ at 0° C. during 3 h with stirring. The reaction mixture was stirred for 16 h at room temperature and washed with water. The organic phase was dried over $Na_2SO_4$, evaporated to dryness in vacuum to obtain 8.0 g of a colorless oil which was purified by silica gel chromatography ($CHCl_3$—MeOH 5:0.1). $^1$H-NMR ($CDCl_3$): 1.17 (2H, $NH_2$), 1.39 (9H, $3CH_3$), 2.74 (t, 2H, $CH_2NH_2$, J=6.0 Hz), 3.10 (q, 2H, $CH_2NH$, J=5.5 Hz), 4.99 (bs, 1H, NH). IR (neat): 3354 (N—H), 2977, 2933 (C—H), 1693 (C=O) $cm^{-1}$.

Step 2. Synthesis of N,N-bis-(2-cyanoethyl)-N-tert-butoxycarbonyl ethylenediamine (3). To a solution of the amine 2 (3.2 g, 20 mmol) in a large excess of acrylonitrile (50 ml, 760 mmol), glacial AcOH (2.3 ml, 40 mmol) was added and the mixture was refluxed for 24 h. The excess of acrylonitrile was evaporated in vacuum to obtain a residue, which was dissolved in $CHCl_3$ (50 ml) and added to 30 ml of concentrated ammonium hydroxide. The organic layer was separated, washed with water and dried over $Na_2SO_4$. After evaporation of the solvent, 4.3 g of yellowish oil was obtained. The oil was purified in silica column chromatography with elute ($CHCl_3$—MeOH 5:0.1). $^1$H-NMR (CDCl$_3$): 1.42 (s, 9H, 3CH$_3$), 2.47 (t, 4H, 2 CH$_2$CN, J=6.6 Hz), 2.65 (t, 2H, N—CH$_2$CH$_2$NH, J=6.0 Hz), 2.87 (t, 4H, 2 CH$_2$N, J=6.0 Hz), 3.18 (q, 2H, NCH$_2$CH$_2$NH, J=6.0 Hz), 4.97 (bs, 1H, NH). IR (neat): 3348 (N—H), 2977, 2947, 2836 (CH$_2$), 2247 (CN), 1692 (C=O) cm$^{-1}$.

Step 3. Synthesis of N,N-bis-(3-aminopropyl)-N-tertbutoxycarbonyl ethylenediamine (4). The 1.33 g (5 mmol) of compound 3, 25 ml of the 1.4 M solution NaOH in 95% EtOH and 1 g of Ni-Raney slurry in water (pH=10.0) were added to a 250 ml hydrogenation vessel. The mixture was placed under hydrogen (40 psi) in a Parr hydrogenation apparatus and shaken for 24 hours at room temperature. The mixture was carefully in vacuum filtered through sintered glass funnel and the catalyst was washed with 95% EtOH. After diluting the filtrate with 20 ml H$_2$O, EtOH was evaporated and the residue was concentrated. After addition of 20 ml of NaOH saturated solution, the amine 4 began to separate as an oil which was extracted with CHCl$_3$. The combined extract was dried over Na$_2$SO$_4$ and the solvent was evaporated to obtain a colorless oil (1.37 g, 5 mmol). $^1$H-NMR (CDCl$_3$): 1.20 (bs, 4H, 2NH$_2$), 1.39 (s, 9H, 3CH3), 1.52 (m, 4H, 2 CH$_2$CH$_2$CH$_2$), 2.45 (t, 6H, CH$_2$N, J=7.1 Hz), 2.67 (t, 4H, 2CH$_2$NH$_2$, J=7.1 Hz), 3.13 (q, 2H, NCH$_2$CH$_2$NH, J=6.0 Hz), 5.22 (bs, 1H, NH). IR (neat): 3371 (N—H), 2973, 2933, 2865 (CH), 1687 (C=O) cm$^{-1}$.

Step 4: Synthesis of 4-cascade-N-tert-butoxycarbonyl ethylenediamine [2]-(1-azabutylidyne)-propanitrile (5). The procedure is similar to that in step 2. The compound 5 was a yellowish oil. $^1$H-NMR (CDCl$_3$): 1.42 (s, 9H, 3CH$_3$), 1.59 (m, 4H, 2CH$_2$CH$_2$CH$_2$), 2.46-2.56 (m, 18H, 9CH$_2$N), 2.82 (t, 8H, 4CH$_2$CN, J=6.6 Hz), 3.14 (q, 2H, CH$_2$NH, J=6.0 Hz), 4.99 (bs, 1H, NH). IR (neat): 3377 (N—H), 2963, 2935, 2825 (C—H), 2247 (CN), 1702 (C=O).

Step 5: Synthesis of 4-cascade-N-tert-butoxycarbonylethylenediamine [2]-(1-azabutylidyne)-propanamine (6). The procedure is similar to that in step 3. The compound 6 was a colorless oil. $^1$H-NMR (CDCl$_3$): 1.40 (m, 17H, 9H, 3CH$_3$, 8H, 4NH$_2$), 1.52 (m, 12H, 6CH$_2$CH$_2$CH$_2$), 2.38 (m, 18H, 9CH$_2$N), 2.68 (t, 8H, 4CH$_2$NH$_2$, J=6.6 Hz), 3.13 (m, 2H, CH$_2$NH), 4.93 (bs, 1H, NH). IR (neat): 3375 (N—H), 2939 (C—H), 1690 (C=O).

Step 6: Synthesis of Compound 7. To the stirred mixture of the amine 6 (1.0 g, 2 mmol) in 50 ml THF, 2.0 g of K$_2$CO$_3$ and 1.93 g of allyl bromide (16 mmol) were added and stirring was continued at room temperature for 36 h. The solution was filtered and washed with CHCl$_3$. After evaporating the solvent, yellowish oil was dissolved in water, adjusted to pH, 8 with NaHCO$_3$ solution, and extracted with CHCl$_3$. The combined extract was washed with 10% brine solution, dried over Na$_2$SO4 and concentrated to afford 1.0 g of a yellowish oil, compound 7. $^1$H-NMR (CDCl$_3$): 1.39-1.54 (21H, 3CH$_3$, 6NCH$_2$CH$_2$CH$_2$N), 2.36-2.47 (26H, 13NCH$_2$), 3.05 (t, 16H, 8NCH$_2$CH=CH$_2$), 3.12 (2H, NHCH$_2$), 5.10 (t, 16H, 8CH=CH$_2$), 5.76-5.82, (m, 8H, 8CH=CH$_2$). IR (neat): 3378 (NH), 3075 (CH=CH$_2$), 2947, 2804(CH$_2$), 1704 (C=O), 1642(C=C)

Step 7: Synthesis of Compound 8. To the compound 7 (1.0 g, 1.2 mmol) dissolved in 10 ml of CH$_2$Cl$_2$, 10 ml of ethyl ether and 5 ml of concentrated HCl were added. After stirring for 4 hours at room temperature, the solvents were removed under vacuum. The resulting residue was dissolved in NaOH and extracted with CH$_2$Cl$_2$. The combined extract was dried over Na$_2$SO4, filtered, and concentrated in vacuum to obtain 0.7 g of an brownish oil. $^1$H-NMR (CDCl$_3$): 1.52-1.54 (12H, 6NCH$_2$CH$_2$CH$_2$N), 2.2-2.5 (26H, 13NCH$_2$), 3.03-3.06 (16H, 8NCH$_2$—CH=CH$_2$), 3.3 (2H, NCH$_2$CH$_2$N), 4.16 (2H, NH$_2$), 5.08-5.10 (16H, 8CH=CH$_2$), 5.77-5.79 (8H, 8CH=CH$_2$). IR (neat): 3389 (NH$_2$), 3075 (CH=CH$_2$), 2946, 2804 (CH$_2$), 1642 (C=C)

Step 8: Synthesis of Compound 9. The procedure is similar to that in step 2.

Step 9: Synthesis of Compound 10, the targeted dendron ligand. The procedure is similar to that in step 3.

All of the publications or patents mentioned herein are hereby incorporated by reference in their entireties. The above examples are merely illustrative of the present invention, and are not intended to limit the scope of the appended claims.

We claim:

1. A method of forming a dendron box comprising:
   contacting a solid nanoparticle core between about 1 nm and about 100 nm in diameter with a plurality of cross-linkable dendron ligands to form a dendron-nanoparticle;
   cross-linking the dendron ligands to form a box-nanoparticle; and
   removing the solid nanoparticle core from the box-nanoparticle to form the dendron box.

2. The method of claim 1, wherein the nanoparticle core comprises a nanocrystal.

3. The method of claim 1, wherein the cross-likable dendron ligands are selected from G3-(hydroxamide)-CH=CH$_2$, G3-(carboxylic)-CH=CH$_2$, G2-(amine)-ester, G3-(thiol)-CH=CH$_2$, G3-(diamine)-OH, G3-(thiol)-OH, G3-(dicarboxylic)-OH/PEG, or G4-(dicaboxylic)-CH=CH$_2$/PEG.

4. The method of claim 1, wherein dendron ligands comprise cross-likable alkene groups prior to cross-linking, and wherein the alkene groups are substantially cross-linked by a ring-closing metathesis reaction.

5. The method of claim 1, wherein the dendron ligands comprise cross-likable groups prior to cross-linking, and wherein the cross-likable groups are substantially cross-linked by a dendrimer bridging reaction using a linker molecule.

6. The method of claim 1, wherein the nanoparticle core comprises a metal, an elemental non-metal, an organic compound, a metal oxide, a metal chalcogenide, a metal pnictogen, a metal halide, an alloy, a mixed metal oxide, or a combination thereof.

7. The method of claim 1, wherein the nanoparticle core comprises a boride, a carbide, a suicide, a nitride, a phosphide, an arsenide, an oxide, a sulfide, a selenide, a telluride, a fluoride, a chloride, a bromide, an iodide, or a combination thereof.

8. The method of claim 1, wherein the nanoparticle core comprises an oxide of silicon, aluminum, titanium, zirconium, iron, nickel, cobalt, manganese, ruthenium, antimony, tin, cerium, barium, vanadium, chromium, lead, copper, indium, yttrium, zinc, mixed oxides thereof, or combinations thereof.

9. The method of claim 1, wherein the nanoparticle core comprises a CdSe nanocrystal, a CdS nanocrystal, or a CdSe/CdS core/shell nanocrystal.

10. The method of claim 1, wherein the nanoparticle core is removed from the solid nanoparticle core is removed from the box-nanoparticle by chemical etching, photochemical etching, thermolysis, or a combination thereof.

* * * * *